United States Patent
Malle et al.

(10) Patent No.: US 10,561,589 B2
(45) Date of Patent: *Feb. 18, 2020

(54) ANHYDROUS SOFT SOLID COMPOSITION BASED ON PARTICLES ENCAPSULATING A BENEFICIAL AGENT

(71) Applicant: L'OREAL, Paris (FR)

(72) Inventors: Gérard Malle, Villiers S/Morin (FR); Tiina Luukas, Sevran (FR); Didier Laverre, Chevilly la Rue (FR); Isabelle Bara, La Verenne St Hilaire (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/324,103

(22) PCT Filed: Jul. 1, 2015

(86) PCT No.: PCT/EP2015/065005
§ 371 (c)(1),
(2) Date: Jan. 5, 2017

(87) PCT Pub. No.: WO2016/005246
PCT Pub. Date: Jan. 14, 2016

(65) Prior Publication Data
US 2017/0189282 A1    Jul. 6, 2017

(30) Foreign Application Priority Data
Jul. 9, 2014 (FR) ...................... 14 56631

(51) Int. Cl.
| | | |
|---|---|---|
| *A61K 8/60* | (2006.01) | |
| *A61K 8/73* | (2006.01) | |
| *A61K 8/92* | (2006.01) | |
| *A61K 8/11* | (2006.01) | |
| *A61Q 13/00* | (2006.01) | |
| *A61Q 15/00* | (2006.01) | |
| *A61K 8/25* | (2006.01) | |
| *A61K 8/34* | (2006.01) | |
| *A61K 8/891* | (2006.01) | |
| *A61K 8/895* | (2006.01) | |
| *A61K 8/02* | (2006.01) | |
| *A61K 8/19* | (2006.01) | |
| *A61K 8/37* | (2006.01) | |
| *A61K 8/44* | (2006.01) | |
| *A61K 8/58* | (2006.01) | |
| *A61K 8/81* | (2006.01) | |

(52) U.S. Cl.
CPC ............. *A61K 8/11* (2013.01); *A61K 8/0216* (2013.01); *A61K 8/19* (2013.01); *A61K 8/25* (2013.01); *A61K 8/34* (2013.01); *A61K 8/345* (2013.01); *A61K 8/37* (2013.01); *A61K 8/44* (2013.01); *A61K 8/585* (2013.01); *A61K 8/60* (2013.01); *A61K 8/732* (2013.01); *A61K 8/738* (2013.01); *A61K 8/8111* (2013.01); *A61K 8/891* (2013.01); *A61K 8/895* (2013.01); *A61Q 13/00* (2013.01); *A61Q 15/00* (2013.01); *A61K 2800/31* (2013.01); *A61K 2800/412* (2013.01)

(58) Field of Classification Search
None
See application file for complete search history.

(56) References Cited

U.S. PATENT DOCUMENTS

| | | |
|---|---|---|
| 5,508,259 A | 4/1996 | Holzner et al. |
| 6,200,949 B1 | 3/2001 | Reijmer et al. |
| 2004/0029750 A1 | 2/2004 | Schudel et al. |

FOREIGN PATENT DOCUMENTS

| | | |
|---|---|---|
| DE | 10-2008-035013 A1 | 1/2010 |
| JP | 2008-156236 A | 7/2008 |

OTHER PUBLICATIONS

EPO English translation of Owaku (JP2008-156236A), pp. 1-26. (Year: 2008).*
Tereos, "Maltodextrins" ([retrieved from on-line website: https://www.tereos-starchsweeteners.com/food-beverages/product-finder/maltodextrin/maltodextrin, 2013, pp. 1-2]). (Year: 2013).*
Jeen International Corporation, "Peppermint Oil MSDS", 1998, pp. 1-2 (Year: 1988).*
Lafaver, "Bulk density and Tapped Density", PHarmacopeial Forum: vol. No. 31(3) p. 909 or USP32-NF p. 206 (Year: 2008).*

(Continued)

*Primary Examiner* — Kyung S Chang
(74) *Attorney, Agent, or Firm* — Polsinelli PC

(57) ABSTRACT

Disclosed is an anhydrous composition comprising particles having a core containing a beneficial agent and an envelope surrounding the core. The envelope comprises a hydrophobically modified polysaccharide and a water-soluble carbohydrate and/or water-soluble polyol. The particles have a poured powder density from 300.0 g/l to 600.0 g/l and an absolute density of greater than 1.0. The composition also comprises a fatty phase comprising a solid fatty substance and an oil. The composition has a hardness measured at 32° C. at a humidity of 40% from 15 kPa to 150 kPa. Also disclosed are uses of the composition for caring for and/or for the hygiene of and/or for conditioning and/or for fragrancing and/or for making up a keratin material. The composition can be used for treating body odor wherein the composition comprises a deodorant active agent and/or antiperspirant active agent in free form and/or in encapsulated form.

19 Claims, No Drawings

(56) References Cited

OTHER PUBLICATIONS

Martin et al., "Encapsulation and Co-Precipitation Process with Supercritical Fluids: Application with Essential Oils", The Open Chemical Engineering Journal, 2010, 4, 31-41.
Carneiro et al., Encapsulation efficiency and oxidative stability of flaxseed oil microencapsulated by spray drying using different combinations of wall materials, Journal of Food Engineering, 115 (2013) 443-451.

* cited by examiner

ANHYDROUS SOFT SOLID COMPOSITION BASED ON PARTICLES ENCAPSULATING A BENEFICIAL AGENT

CROSS REFERENCE TO RELATED APPLICATIONS

This application is a National Phase filing under 35 U.S.C. § 371 of PCT/EP2015/065005 filed on Jul. 1, 2015; and this application claims priority to Application No. 1456631 filed in France on Jul. 9, 2014 under 35 U.S.C. § 119. The entire contents of each application are hereby incorporated by reference.

The present invention relates to an anhydrous composition comprising:

1) at least particles comprising a core containing at least one beneficial agent and an envelope surrounding the core; said envelope comprising at least one hydrophobically modified polysaccharide and at least one water-soluble carbohydrate and/or water-soluble polyol;

said particles simultaneously having a poured powder density ranging from 300.0 g/l to 600.0 g/l and an absolute density of greater than 1.0 and 2) at least one fatty phase comprising at least one solid fatty substance and at least one oil;

said composition having a hardness measured at 32° C. at a humidity of 40% ranging from 15 kPa to 150 kPa and preferably ranging from 20 kPa to 100 kPa.

The invention also relates to a cosmetic process for caring for and/or for the hygiene of and/or for conditioning and/or for fragrancing and/or for making up a keratin material, which consists in applying to said keratin material a composition as defined previously.

The invention also relates to a cosmetic process for treating body odor and optionally human perspiration, which consists in applying to a keratin material a composition as defined previously comprising at least one deodorant active agent and/or antiperspirant active agent in free form (not encapsulated) and/or in encapsulated form.

Many presentation forms allow the dispensing of beneficial agents, especially of cosmetic or pharmaceutical products, fragrancing products, veterinary products, especially animal hygiene and/or care products; household maintenance products such as laundry care products (stain removers), maintenance products for domestic electrical appliances, maintenance products for floors, tiles, wood, etc.; textile maintenance products, maintenance products for leather goods such as shoes and soles; maintenance products in the motor vehicle industry. Among these, "soft solid" compositions constitute a category of products that is appreciated by consumers for their efficacy and, especially in the cosmetics industry, for their sensory qualities (soft, dry feel). They are likened to solid compositions that soften under the effect of a stress such as spreading over the surface of the skin or, for example, by extrusion through a device with an openwork wall (grille).

They are especially used in the cosmetic field, in particular in the field of deodorants and antiperspirants, but may also be of increased value in other cosmetic fields such as products for caring for keratin materials such as the skin, the hair or the lips, for instance massage products, balms, ointments, creams or gels intended for topical application to the skin or to the hair.

The aim of the present invention is to propose novel compositions of anhydrous "soft solid" type comprising at least one beneficial agent encapsulated in particles that are leaktight in the absence of moisture, i.e. odorless if the active agent is a perfume said particles having a low poured powder density to facilitate their formulation said particles also needing to be compatible with the usual ingredients of these formulations and strong enough to be able to be formulated as "soft solid" without being damaged said beneficial agent contained in the particles being able to be released virtually immediately, gradually and repeatably on the skin, the hair and the integuments on contact with water.

It is known that there is a need in many industrial fields to protect a certain number of fragile or volatile molecules and to control their release into an external medium.

One of the means for achieving such an aim is to encapsulate them. The object of this encapsulation is to reduce the evaporation and the transfer of the active material toward the environment, either during storage or during the production of the products, or alternatively during their use. Said encapsulation may also make the material easier to use by diluting it and by promoting its uniform distribution in the support.

Microencapsulation includes all the technologies for coating or trapping active principles in solid, liquid or gaseous form inside individualized particles whose size ranges between a few microns and a few millimeters. If these microparticles are hollow (vesicular), they are referred to as microcapsules, and if they are filled (matrix-based), they are referred to as microspheres. Their size ranges from 1 µm to more than 1000 µm. These microparticles may or may not be biodegradable and may contain between 5% and 90% (by mass) of active substance.

The encapsulated active substances are of very varied origin: pharmaceutical or cosmetic active principles, food additives, plant protection products, fragranced essences, microorganisms, cells, or alternatively chemical reaction catalysts, etc.

The entire advantage of encapsulation microparticles lies in the presence of a polymer membrane, which isolates and protects the contents from the external medium. Depending on the case, the membrane will be destroyed during use to release its contents (for example: "scratch and sniff" advertising inserts which release perfume when the microcapsules are crushed), or alternatively the membrane will remain present throughout the release of the contents, the rate of diffusion of which it will control (for example: encapsulation of medicaments for sustained release).

The coating materials are generally hydrophobic or hydrophilic polymers of natural or synthetic origin, or alternatively lipids.

The main processes for performing the encapsulation of substances in microparticles are interfacial polymerization, interfacial crosslinking, emulsification followed by evaporation or extraction of the solvent, double emulsification evaporation/extraction of solvent, spray-drying, prilling and coacervation.

U.S. Pat. No. 5,508,259 proposes nonaqueous fragrancing compositions, comprising perfumes encapsulated in water-soluble capsules. Said capsules are obtained via conventional encapsulation techniques and in particular the spray-drying of an emulsion formed from a film-forming solid substrate in combination with an emulsifying agent and a mixture of fragrancing ingredients. The film-forming solid substrate is especially chosen from polyvinyl acetate, polyvinyl alcohol, dextrins, natural or modified starch, plant gums, pectins, xanthans, alginates, carrageenans or alternatively cellulose derivatives, for instance carboxymethylcellulose, methylcellulose or hydroxyethylcellulose. The emulsion is then dehydrated via a standard atomization (spray-drying) process, which consists, as described in Example 1, in spraying it as fine droplets in an atomizer at a flow rate of 50 kg/h and a pressure of 0.45 bar, in contact with an air stream at 320 m$^3$/h heated to 350° C. so as to evaporate the water, which makes it possible to obtain a fine powder with a particle diameter of between 20 and 80 microns and containing 20% by weight of perfume.

However, it was noted that the particles obtained via this process were highly odorous in dry form on account of the presence of free (non-encapsulated) perfume, that they were formed mainly from agglomerates that were liable to harm the homogeneity of the product and prevent correct application of the product, and that they did not have the density characteristics suitable for the objective of the invention.

U.S. Pat. No. 6,200,949 also describes a process for forming a particulate material containing a hydrophilic perfume, comprising the successive steps consisting in forming an aqueous emulsion of perfume containing 40% to 60% by weight of water, 3% to 30% by weight of maltodextrin and 10% to 40% by weight of hydrophobically modified starch, and then in drying it by spraying in an atomizer (air stream of 420 m$^3$/h heated to 204° C.) so that the particles are formed with a mean size of from about 3 to about 10 microns and a perfume content of from 15% to 50% by weight. However, the particles obtained via this process are highly odorous in dry form on account of the presence of free (non-encapsulated) perfume, they are formed mainly from agglomerates, are liable to harm the homogeneity of the product and do not have the density characteristics suitable for the objective of the invention.

It is thus very important to be able to provide leaktight encapsulation particles which release their contents only on demand (in response to the ambient moisture, especially in humid climatic zones, for example in response to body perspiration, shampooing or showering, etc.), firstly to ensure protection over time of the encapsulated active agent, above all if it is fragile and/or volatile, and secondly to avoid interactions with the other ingredients of the formulation. When the encapsulated beneficial agent is a fragrancing ingredient and/or a whole perfume, it is all the more important for the encapsulation to be total, which leads to odorless particles in anhydrous formulations allowing the formulator to combine them, if desired, with any free perfume of his choice (identical or different) without any risk of interactions or of disruption of the chosen fragranced note.

Patent EP 1 917 098 B1 proposes a process for preparing encapsulation particles by precipitation, said process using:
a pumpable emulsion comprising (i) a continuous phase containing a solvent and a solute forming a matrix dissolved in said solvent and (ii) a dispersed phase;
an extractor comprising a supercritical, subcritical or liquefied gas; said solvent being substantially more soluble in the extractor than said solute forming a matrix, and said process comprising the successive steps consisting in:
a. combining the pumpable emulsion with the extractor under mixing conditions;
b. allowing the formation of particulate encapsulation products in which the dispersed phase is embedded in a solid matrix of the solute forming a matrix;
c. collecting the encapsulation products and separating them from the extractor.

It is indicated that this process may be used in the pharmaceutical and agrifood industries and also in the fields of agriculture, coating, adhesives and catalysts. It may be used in particular for encapsulating pharmaceutical active agents, flavorings, enzymes, dyes, pesticides and herbicides.

After extensive research, the Applicant has discovered, surprisingly and unexpectedly, that it is possible to achieve the objectives as stated previously by using, in a soft solid anhydrous composition comprising at least one solid fatty substance and at least one oil, particles comprising a core containing at least one beneficial agent and an envelope surrounding the core; said envelope comprising at least one hydrophobically modified polysaccharide and at least one water-soluble carbohydrate and/or water-soluble polyol; said particles simultaneously having a poured powder density ranging from 300.0 g/l to 600.0 g/l and an absolute density of greater than 1.0. These particles may be obtained in particular via the process as described in patent EP 1 917 098 B1 commented previously.

The particles in accordance with the present invention make it possible to encapsulate beneficial ingredients, which are in particular fragile, completely (total encapsulation), without degradation, in capsules that are strong enough and leaktight enough to be able to be stored without impairment in the absence of moisture, and which can be readily formulated and remain stable in soft solid anhydrous compositions. These same particles of this type of composition preferably have spherical morphology and a very low poured powder density to conserve the light and soft texture; they also have the capacity of opening in the presence of water to be able to release their beneficial agent virtually immediately, gradually and repeatably on the skin, the hair and the integuments on contact with water.

This discovery forms the basis of the present invention.

The present invention relates to an anhydrous composition comprising:

1) at least particles comprising a core containing at least one beneficial agent and an envelope surrounding the core; said envelope comprising at least one hydrophobically modified polysaccharide and at least one water-soluble carbohydrate and/or water-soluble polyol;
said particles simultaneously having a poured powder density ranging from 300.0 g/l to 600.0 g/l and an absolute density of greater than 1.0 and 2) at least one fatty phase comprising at least one solid fatty substance and at least one oil;
said composition having a hardness measured at 32° C. and at a humidity of 40% ranging from 15 kPa to 150 kPa and preferably ranging from 20 kPa to 100 kPa.

Preferably, the composition comprises a physiologically acceptable medium.

According to a particular form of the invention, the compositions of the invention are cosmetic or dermatological.

According to a particular form of the invention, the compositions according to the invention may be used in other industrial applications and may especially be consumer products chosen from veterinary products, especially animal hygiene and/or care products; household maintenance products such as laundry care products (stain removers), maintenance products for domestic electrical appliances, maintenance products for floors, tiles, wood, etc.; textile maintenance products, maintenance products for leather goods such as shoes and soles; maintenance products in the motor vehicle industry.

The invention also relates to a cosmetic process for caring for and/or for the hygiene of and/or for conditioning and/or for fragrancing and/or for making up a keratin material, which consists in applying to said keratin material a composition as defined previously.

The invention also relates to a cosmetic process for treating body odor and optionally human perspiration, which consists in applying to a keratin material a composition as defined previously comprising at least one deodorant active agent and/or antiperspirant active agent in free form and/or in encapsulated form.

The invention also relates to a consumer product, characterized in that it is formed from a composition as defined previously.

Definitions

For the purposes of the present invention, the term "anhydrous composition" means a composition with a water content of less than 5% by weight, preferably less than 2% by weight and even more preferably less than 1% by weight relative to the weight of said composition, or alternatively even less than 0.5% and especially free of water. In this definition, the water mentioned includes the residual water provided by the mixed ingredients.

For the purposes of the present invention, the term "physiologically acceptable medium" is intended to denote a medium that is suitable for the topical administration of a composition. A physiologically acceptable medium is a medium which has no unpleasant odor and/or appearance, and which is perfectly compatible with topical administration.

The term "keratin material" means the skin, the scalp, the lips and/or integuments such as the nails and keratin fibers, for instance bodily hair, the eyelashes, the eyebrows and head hair.

For the purposes of the invention, the term "cosmetic composition" means any composition applied to a keratin material to produce a non-therapeutic hygiene, care, conditioning or makeup effect contributing toward improving the well-being and/or enhancing the beauty and/or modifying the appearance of the keratin material onto which said composition is applied.

For the purposes of the invention, the term "dermatological composition" means any composition applied to a keratin material to prevent and/or treat a disorder or dysfunction of said keratin material.

For the purposes of the invention, the term "cosmetic treatment" means any non-therapeutic fragrancing, hygiene, care, conditioning or makeup effect contributing toward improving the well-being and/or enhancing the beauty and/or modifying the appearance or odor of the keratin material onto which said composition is applied.

The term "consumer product" means any manufactured product intended to be used or consumed in the form in which it is sold and which is not intended for a subsequent manufacture or modification. Without the examples being limiting, the consumer products according to the invention may be cosmetic products also including cosmetic formulations for caring for and/or for the hygiene of and/or for making up the skin, the lips, the nails, the eyelashes, the eyebrows, the hair or the scalp; dermatological products; fragrancing products; pharmaceutical products; products for veterinary use, especially animal hygiene and/or care products; household maintenance products such as laundry care and/or cleaning products (stain removers); products for maintaining domestic electrical appliances; products for maintaining floors, tiles, wood, etc.; sanitary products; textile maintenance products; maintenance products in leather goods such as shoes and soles; maintenance products in the motor vehicle industry.

For the purposes of the invention, the term "beneficial agent" means any compound present in a consumer product which produces a beneficial effect perceived by the consumer during its use and/or obtained on the consumer product itself, said beneficial effect possibly being a sensory improvement or a modification, which is especially visual and/or olfactory and/or tactile, an improvement in the comfort and/or ease of application, an esthetic effect, a hygiene effect, a sensation of cleanliness, or a curative and/or prophylactic effect. The term "particles comprising a core containing at least one beneficial agent" means a particle comprising at least one beneficial agent which is immobilized, captured and/or encapsulated in the matrix of an encapsulation or trapping system; said beneficial agent being released to the exterior gradually as the encapsulation or trapping system deteriorates when its degradation takes place on contact with a medium with which it reacts or under the effect of a stimulus such as a supply of water.

Poured Powder Density (or Loose Bulk Density)

The determination is performed at room temperature (20-25° C.) and under normal atmospheric conditions (1 atmosphere) using a 100 ml measuring cylinder. The measuring cylinder is weighed empty and then filled with a volume of 100 ml of poured powder, without tapping. The difference in mass between the empty measuring cylinder and the cylinder filled with 100 ml of powder gives the poured powder density.

Absolute Density

Measurement Principle

The measurement consists in determining the weight of a sample of the solid powder by simple weighing, followed by measuring the volume occupied by the powder particles by measuring the volume of liquid displaced by the powder sample by immersion in this liquid. The liquid chosen must be sparingly volatile and must not be a solvent for the powder. Cyclohexane is generally chosen. The measurements are performed at least twice.

Materials: A 10 or 25 ml graduated flask and a precision balance.

$m_1$ is the weight of the empty flask.

$m_2$ is the weight of the flask filled with water up to the graduation mark.

$m_3$ is the weight of the flask filled with cyclohexane up to the graduation mark.

$m_4$ is the weight of the flask filled to about one third of its volume with the powder to be analyzed.

The flask is filled to about one third of its volume with the powder to be analyzed.

Method

The flask is filled to slightly below the graduation mark with cyclohexane. In order to completely remove the air trapped in the powder, the following are performed:

1) the flask is treated in an ultrasonic bath for 5 minutes
2) the level of cyclohexane is adjusted to the graduation mark
3) the flask is treated in an ultrasonic bath for 2 minutes
4) steps 2 and 3 are repeated if necessary, until the level of the cyclohexane no longer changes.

$m_5$ is the weight of the flask thus filled.

The weight of powder analyzed is equal to $m_4-m_1$ (for good accuracy, this weight must be greater than 2 g). Since the density of air is very low relative to that of the solid, it is taken that $m_4-m_1$ is equal to the weight of the constituent solid of the powder.

The weight of cyclohexane corresponding to the volume occupied by the solid (Vs) is equal to:

$m_6=(m_3-m_1)-(m_5-m_4)=\rho_{cyclo}\cdot Vs$ where $\rho_{cyclo}$ is the density of cyclohexane at the temperature of the laboratory.

The absolute density of the constituent solid of the powder is equal to $\rho_{cyclo}=(m_4-m_1)/Vs=\rho_{cyclo}(m_4-m_1)/m_6$.

If the density of cyclohexane at the temperature of the laboratory is unknown, it is determined as follows relative to that of water:

If Vf is the graduated volume of the flask and $\rho_{water}$ is the density of water at the temperature of the laboratory, then:

$\rho_{cyclo}=(m_3-m_1)/Vf$ and $\rho_{water}=(m_2-m_1)/Vf$ i.e. $\rho_{cyclo}=\rho_{water}(m_2-m_1)/(m_3-m_1)$ The absolute density of the constituent solid of the powder is equal to:

$\rho_5=[\rho_{water}(m_4-m_1)(m_2-m_1)]/[m_6(m_3-m_1)]$.

Hardness

The compositions according to the invention that are termed "soft solids" have a hardness measured at 32° C. and at a humidity of 40% ranging from 15 kPa to 150 kPa and preferably ranging from 20 kPa to 100 kPa.

The hardness is defined as the maximum stress force Fmax measured by texturometry during the penetration of a cylindrical probe into the formulation sample, assessed under precise measurement conditions as follows.

The formulations are poured hot into jars 9 cm in diameter and 3 cm deep (i.e.: "Favorit Soft" jars from RPC Bramlage GmbH). Cooling is performed at room temperature. The hardness of the formulations produced is measured after an interval of 24 hours. The jars containing the samples are characterized by texturometry using a texturometer such as the TA-XT2 machine sold by the company Rheo, according to the following protocol:

At a temperature of 32° C. and at a relative humidity of 40%, a cylindrical stainless-steel probe with a spindle 2 mm in diameter is brought into contact with the sample at a speed of 1 mm/s. The measurement system detects the interface with the sample, with a detection threshold equal to 0.005 newton. The probe penetrates 0.3 mm into the sample, at a speed of 0.1 mm/s. The measuring machine records the change in force measured in compression over time, during the penetration phase. The hardness of the sample corresponds to the average of the maximum force values detected during penetration, over at least three measurements. After a measurement, the relaxation time is 1 second, and the probe is withdrawn at a speed of 1 mm/s.

The hardness of the composition is calculated via the following equation:

$$\text{hardness} = \frac{F_{max}}{\text{Area of the cyclinder}}$$

Encapsulation Particles

The particles in accordance with the invention comprise a core containing at least one beneficial agent and an envelope surrounding the core; said envelope comprising at least one hydrophobically modified polysaccharide and at least one water-soluble carbohydrate and/or a water-soluble polyol; said particles simultaneously having a poured powder density ranging from 300.0 g/l to 600.0 g/l and an absolute density of greater than 1.0.

The particles in accordance with the present invention are preferably spherical.

The term "spherical" means that the particle has a sphericity index, i.e. the ratio between its largest diameter and its smallest diameter, of less than 1.2. In this case, such particles are generally referred to as "capsules".

The term "mean size" of the particles means the parameters D[4,3] and D[2,3] measured via the dry route by laser scattering using a Microtrac S3500 particle size analyzer, the results being expressed in the form of the volume and number particle size distributions giving access to the mean diameter.

The spherical particles in accordance with the present invention thus preferably have a number-mean diameter ranging from 1 to 30 μm, more preferentially ranging from 2 to 15 μm and even better still from 5 to 10 μm and a volume-mean diameter ranging from 5 to 150 μm, preferably ranging from 10 to 100 μm and even better still from 20 to 80 μm.

The particles according to the invention containing the beneficial agent preferably represent from 0.1% to 60% by weight, preferably from 0.3% to 40% by weight and better still from 0.5% to 20% by weight relative to the total weight of the composition.

Hydrophobically Modified Polysaccharide

The term "hydrophobically modified polysaccharide" means any chemically or enzymatically modified polysaccharide comprising at least one hydrophobic functional group.

Polysaccharides are carbohydrate macromolecules formed by the linking of a large number of hydrophilic elementary sugars (saccharides) bonded together via O-oside bonds.

The hydrophobic functional groups of the present invention are hydrocarbon-based groups (formed essentially from carbon and hydrogen atoms) comprising at least 4 carbon atoms, preferably at least 6 and better still at least 8 carbon atoms, such as alkyl, alkenyl, aryl (i.e. phenyl) or aralkyl (i.e. benzyl) groups. The maximum number of carbon atoms in the hydrocarbon-based group is preferably 24, more preferentially 20 and even more preferentially 18. The hydrophobic hydrocarbon-based groups may be unsubstituted, for example formed from a simple long alkyl chain, or may be substituted with unreactive groups, for instance aromatic groups such as aryl (i.e. phenyl) or aralkyl (i.e. benzyl) groups or alternatively polar groups, for instance carboxyls or hydroxyls.

To graft the hydrophobic functional group(s) onto the polysaccharides, use is generally made of halogenated derivatives, epoxides, isocyanates, or carboxylic acids or derivatives thereof (esters, acid halides or anhydrides).

Among the hydrophobically modified polysaccharides according to the invention, preference is given to hydrophobically modified neutral polysaccharides such as:

cellulosas and derivatives thereof, in particular hydrophobically modified methyl-, hydroxyethyl-, ethylhydroxyethyl-, hydroxypropyl-, hydroxypropylm ethyl- and carboxymethyl-celluloses. The preferred hydrophobic groups are chosen from $C_8$-$C_{18}$ alkyl radicals and more particularly $C_{12}$-$C_{18}$ alkyl radicals. In particular, the hydrophobically modified neutral polysaccharides denote hydrophobically modified ethylhydroxyethylcellulose or hydroxyethylcellulose and especially those sold by Ashland under the trade name Natrosol Plus;

hydrophobically modified starches and derivatives thereof (in particular: hydroxyethyl-, hydroxypropyl- and carboxymethyl-starch) and also hydrophobically modified degraded and/or esterified starches, hydrophobically modified dextrans especially such as the phenoxy-dextrans obtained by reaction between 1,2- epoxy-3-phenoxypropane and a dextran; ($C_6$-$C_{12}$) alkyl-dextrans obtained by reaction between 1,2-epoxy-($C_6$-$C_{12}$)alkanes such as 1,2-epoxyoctane or 1,2-epoxydodecane and a dextran;

hydrophobically modified guars and hydroxyethyl-, carboxymethyl- and hydroxypropyl-guar derivatives thereof;

hydrophobically modified pullulans such as cholesteryl-pullulans;

inulins hydrophobically modified via alkyl ether, ester and carbamate functions, in particular carbamates bearing $C_4$-$C_{18}$ alkyl chains and more particularly those sold under the name Inutech® SP1.

The hydrophobically modified polysaccharide preferably represents from 20% to 90% by weight, especially from 30% to 80% by weight, better still from 40% to 70% by weight and even better still from 40% to 60% by weight relative to the total weight of the envelope of the particle.

According to a particularly preferred form of the invention, hydrophobically modified starches will be chosen from among the hydrophobically modified polysaccharides.

The botanical origin of the starch molecules may be cereals or tubers. Thus, the starches are chosen, for example, from corn starch, rice starch, cassava starch, tapioca starch, barley starch, potato starch, wheat starch, sorghum starch and pea starch.

The term "hydrophobically modified starch" means any chemically or enzymatically modified starch comprising at least one hydrophobic functional group.

The hydrophobically modified starches in accordance with the invention are preferably chosen from $C_{10}$-$C_{18}$ hydroxyethyl starch esters and starch $C_5$-$C_{20}$-alkyl or $C_5$-$C_{20}$ alkenyl succinates, more particularly $C_5$-$C_{20}$-alkenyl succinates and even better still sodium starch octenyl succinate (E1450—CAS 66829-29-6/52906-93-1/70714-61-3), in particular the product sold by National Starch under the name Capsul®.

Mention may also be made of the commercial references Capsul TA®, N-LOK®, N-LOK 1930®, HI-CAP 100®, Purity Gum 1773® and Purity Gum 2000® from National Starch, Cleargum CO® from the company Roquette and Emcap®, Emtex® and Delitex from the company Cargill.

Water-Soluble Carbohydrate or Polyol

The term "water-soluble carbohydrate" or "water-soluble polyol" refers to a carbohydrate or a polyol which, when introduced into water without pH modification at 25° C., at a mass concentration equal to 3%, makes it possible to obtain a macroscopically homogeneous and transparent solution, i.e. a solution with a minimum light transmittance value, at a wavelength equal to 500 nm, through a sample 1 cm thick, of at least 80% and preferably of at least 90%.

The term "carbohydrates" (also known as saccharides) means all simple sugars or oses and combinations thereof or osides.

Carbohydrates usually comprise:

(1) monosaccharides or oses which are of two types: aldoses comprising an aldehyde function on the first carbon and ketoses comprising a ketone function on the second carbon. They are also distinguished according to the number of carbon atoms they contain.

(2) oligosaccharides (or oligosides), which are saccharide oligomers bearing a sequence of 2 to 10 monosaccharide units linked via glycoside bonds.

(3) polyholosides (or polysaccharides or polyosides), which are saccharide polymers bearing a sequence of more than 10 monosaccharide units.

Water-Soluble Carbohydrates (1) Saccharides or Monosaccharides

Among the saccharides or monosaccharides that may be used according to the invention, mention may be made, alone or as mixtures, of:

tetroses containing four carbons: erythrose, threose, erythrulose;

pentoses containing five carbons: ribose, arabinose, xylose, deoxyribose;

hexoses containing six carbons: glucose, mannose, fucose, gulose, idose, galactose, talose, fuculose, fructose, sorbose, rhamnose;

heptoses containing seven carbons: sedoheptulose in the D and/or L form thereof.

Among the monosaccharides, use will be made more preferentially of arabinose, xylose, fructose, glucose, mannose, rhamnose or threose and even more preferentially glucose or threose.

(2) Oligosaccharides

Among the oligosaccharides that may be used according to the invention, mention may be made of:

(i) disaccharides or diholosides or diosides composed of two saccharide molecules.

Among the disaccharides, mention may be made of: cellobiose, isomaltose, isomaltulose, lactose, lactulose, maltose, sucrose, trehalose or melibiose.

(ii) triholosides composed of three saccharide molecules, for instance: raffinose or maltotriose.

(iii) dextrins, which are mixtures of linear glucose oligosides in which the glucose units are linked via oside bonds of the α-(1,4) or α-(1,6) type.

(iv) glucose syrups obtained by acidic or enzymatic hydrolysis of starch, the D.E. of which is between 20 and 100.

D.E. or "dextrose equivalent" is the indicator of the degree of hydrolysis of starch.

The higher the D.E., the more extensive the hydrolysis, and thus the higher the proportion of simple (short-chain) sugars.

(v) glucose-fructose syrups especially with a high content of fructose (HFCS: high-fructose corn syrup), which denote a series of corn syrups that have been subjected to enzymatic processes in order to increase their fructose content before being mixed with glucose syrup to obtain their final composition.

Among the glucose-fructose syrups, also known as isoglucose syrups, which may be used according to the invention, mention may be made of:

HFCS 90, which contains 90% fructose and 10% glucose syrup;

HFCS 55, which contains 55% fructose and 45% glucose syrup;

HFCS 42, which contains 42% fructose and 58% glucose syrup.

Among the oligosaccharides, use will be made more preferentially of cellobiose, maltose, isomaltose, raffinose and glucose syrups, more particularly glucose syrups.

Use will be made preferentially of a glucose syrup with a D.E. ranging from 21 to 60 and even more preferentially a glucose syrup with a D.E. of from 21 to 38, for instance the dehydrated glucose syrups sold by Tereos under the names G210, G290 and G380.

(3) Polysaccharides or Polyholosides

Examples that may be mentioned include:

dextrans, which are composed of D-glucose units linked via an α(1-6) oside bond and bearing branches formed from alpha-1,2 or 1,3 or 1,4 bonds. They are prepared by fermentation of beet sugar solely containing hydroxyl groups. It is possible to obtain dextran fractions of different molecular weights from native dextran by hydrolysis and purification. The dextran may in particular be in the form of dextran sulfate.

pullulans, which are formed from maltotriose units, known under the name α(1,4)-α(1,6)-glucan. Three glucose units in maltotriose are connected via an α-(1,4) glycoside bond, whereas the consecutive maltotriose units are connected to each other via an α-(1,6) glycoside bond. It is produced from starch by the fungus *Aureobasidium pullulans*. Pullulan is produced, for example, under the reference Pullulan PF 20® by the group Hayashibara in Japan.

maltodextrins, which are the result of hydrolysis of a cereal (i.e.: wheat, corn) starch or of a tuber (i.e.: potato) starch. They are formed from various sugars (i.e.: glucose, maltose, maltotriose, oligosaccharides and polyosides) derived directly from this reaction, in proportions which depend on the degree of hydrolysis. This degree is measured by the "dextrose equivalent", or D.E., dextrose or D-glucose being the result of a total hydrolysis of starch. The higher the D.E., the more extensive the hydrolysis, and thus the higher the proportion of simple (short-chain) sugars of which maltodextrin is composed.

The maltodextrins used in accordance with the invention preferentially have a D.E. ranging from 4 to 20 and better still maltodextrins with a D.E. ranging from 12 to 20.

Use will preferably be made of potato or corn maltodextrins such as those sold under the trade names MD 20P® from Avebe and Maldex 120®, Maldex 170® and Maldex 190® from Tereos.

Polyols

For the purposes of the invention, polyols are linear, branched and/or cyclic, non-glycoside, saturated or unsaturated carbon-based and especially hydrocarbon-based compounds, comprising 4 to 18 carbon atoms, especially 4 to 16, or even 4 to 12 carbon atoms, and 3 to 9 hydroxyl (OH) groups, and also possibly comprising one or more oxygen atoms intercalated in the chain (ether function).

The polyols in accordance with the invention are preferably linear or branched saturated hydrocarbon-based compounds, comprising 4 to 18 carbon atoms, especially 4 to 16 or even 4 to 12 carbon atoms, and 3 to 9 hydroxyl (OH) groups.

They may be chosen, alone or as mixtures, from:
triols, such as trimethylolethane or trimethylolpropane;
tetraols such as pentaerythritol (tetramethylolmethane), erythritol, diglycerol or ditrimethylolpropane;
pentols such as arabitol;
hexols such as dulcitol, sorbitol, mannitol, dipentaerythritol or triglycerol;
heptols such as volemitol;
octaols;
nonanols such as isomalt, maltitol, isomaltitol or lactitol.

Preferably, the polyol is chosen from sorbitol, maltitol, mannitol and isomalt, and mixtures thereof.

Among the water-soluble carbohydrates and water-soluble polyols in accordance with the invention, the ones that will more particularly be chosen are water-soluble oligo- and polysaccharides and more preferentially dextrans, pullulans, glucose syrups and maltodextrins and better still glucose syrups with a D.E. ranging from 21 to 38 and/or maltodextrins with a D.E. ranging from 4 to 20 and better still maltodextrins with a D.E. ranging from 12 to 20.

Use will preferably be made of glucose syrups such as those sold by Tereos under the names G210, G290 and G380 and potato or corn maltodextrins such as those sold under the trade names MD 20P® from Avebe and Maldex 120®, Maldex 170® and Maldex 190® from Tereos.

The water-soluble carbohydrate(s) and/or polyol(s) in accordance with the invention represent from 10% to 80% by weight, preferably from 15% to 70% by weight, more preferentially from 20% to 65% by weight and better still from 40% to 60% by weight relative to the total weight of the envelope of the particle.

According to a particularly preferred form of the invention, the envelope of the particles according to the invention is formed from
at least one starch ($C_5$-$C_{20}$)alkenyl succinate and
at least one maltodextrin with a D.E. ranging from 4 to 20 and preferably ranging from 12 to 20 and/or a glucose syrup with a D.E. ranging from 21 to 60 and preferentially from 21 to 38.

According to a first variant, the envelope of the particles according to the invention is formed from at least one starch ($C_5$-$C_{20}$)alkenyl succinate and from at least one maltodextrin with a D.E. ranging from 4 to 20 and preferably ranging from 12 to 20.

According to a second variant, the envelope of the particles according to the invention is formed from at least one starch ($C_5$-$C_{20}$)alkenyl succinate and from at least one glucose syrup with a D.E. ranging from 21 to 60 and preferentially ranging from 21 to 38.

According to a particularly preferred form of the invention, the envelope of the encapsulation particles is formed from
a) at least one starch ($C_5$-$C_{20}$)alkenyl succinate in an amount ranging from 20% to 90% by weight, especially from 30% to 80% by weight, preferably from 40% to 70% by weight and better still from 40% to 60% by weight relative to the total weight of the envelope of the particle and
b) at least one glucose syrup with a D.E. ranging from 21 to 38 and/or a maltodextrin with a D.E. ranging from 4 to 20 in an amount ranging from 10% to 80% by weight, preferably from 15% to 70% by weight, more preferentially from 20% to 65% by weight and better still from 40% to 60% by weight relative to the total weight of the envelope of the particle.

According to a particularly preferred form of the invention, the envelope of the encapsulation particles is formed from
a) at least one starch ($C_5$-$C_{20}$)alkenyl succinate in an amount ranging from 20% to 90% by weight, especially from 30% to 80% by weight, preferably from 40% to 70% by weight and better still from 40% to 60% by weight relative to the total weight of the envelope of the particle and
b) at least one maltodextrin with a D.E. ranging from 4 to 20 in an amount ranging from 10% to 80% by weight, preferably from 15% to 70% by weight, more preferentially from 20% to 65% by weight and better still from 40% to 60% by weight relative to the total weight of the envelope of the particle.

According to a particularly preferred form of the invention, the envelope of the encapsulation particles is formed from
a) at least one starch ($C_5$-$C_{20}$)alkenyl succinate in an amount ranging from 20% to 90% by weight, especially from 30% to 80% by weight, preferably from 40% to 70% by weight and better still from 40% to 60% by weight relative to the total weight of the envelope of the particle, and
b) at least one glucose syrup with a D.E. ranging from 21 to 38 in an amount ranging from 10% to 80% by weight, preferably from 15% to 70% by weight, more preferentially from 20% to 65% by weight and better still from 40% to 60% by weight relative to the total weight of the envelope of the particle.

Process for Preparing the Particles with Release of Beneficial Agent

The particles according to the invention may especially be prepared according to the process described in patent EP 1 917 098 B1 from FeyeCon.

According to a particular form of the invention, the particles are obtained according to a process comprising at least the following steps:

an aqueous solution formed from a mixture of the water-soluble carbohydrate and/or the water-soluble polyol and of the hydrophobically modified polysaccharide is prepared, the beneficial agent is then added and the whole is stirred so as to form an emulsion; and said emulsion thus formed is homogenized at high pressure at a pressure ranging from 10 to 200 bar and more preferentially from 20 to 200 bar;

said emulsion is sprayed, preferably continuously, in a drying chamber; and the water is extracted for a time preferably not exceeding 3 hours, and more preferentially not exceeding 30 minutes, with a fluid under pressure such as carbon dioxide, preferably in supercritical form, preferably at a pressure of at least 0.3 XPc and at a temperature of at least Tc−60° C. with Pc corresponding to the critical pressure of the gas and Tc the critical temperature of the gas, so as to obtain particles, which are preferably spherical, with a mean size preferably ranging from 1 to 150 μm, more preferentially ranging from 2 to 100 μm and better still from 5 to 80 μm.

Oily Phase

The oily phase present in the compositions according to the invention comprises at least one oil and at least one solid fatty substance.

The term "oily phase" generally refers to a water-immiscible organic liquid phase. This phase generally comprises one or more hydrophobic compounds which render said phase water-immiscible. Said phase is liquid (in the absence of structuring agent) at room temperature (20-25° C.).

Oils

The term "oil" means a fatty substance that is liquid at room temperature (25° C.) and atmospheric pressure (760 mmHg, i.e. $10^5$ Pa). The oil may be volatile or nonvolatile.

For the purposes of the invention, the term "volatile oil" means an oil that is capable of evaporating on contact with the skin or the keratin fiber in less than one hour, at room temperature and atmospheric pressure. The volatile oils of the invention are volatile cosmetic oils, which are liquid at room temperature, having a nonzero vapor pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "nonvolatile oil" means an oil that remains on the skin or the keratin fiber at room temperature and atmospheric pressure for at least several hours, and that especially has a vapor pressure of less than $10^{-3}$ mmHg (0.13 Pa).

The oils in accordance with the invention are preferably chosen from volatile or nonvolatile mineral, animal, plant and synthetic oils, especially chosen from hydrocarbon-based oils, fluoro oils and silicone oils, and mixtures thereof.

The term "hydrocarbon-based oil" means an oil mainly comprising carbon and hydrogen atoms and possibly one or more functions chosen from hydroxyl, ester, ether and carboxylic acid functions. Generally, the oil has a viscosity of from 0.5 to 100 000 mPa·s, preferably from 50 to 50 000 mPa·s and more preferably from 100 to 300 000 mPa·s.

The term "silicone oil" means an oil comprising in its structure carbon atoms and at least one silicon atom.

The term "fluoro oil" means a partially hydrocarbon-based and/or silicone-based oil comprising carbon atoms and fluorine atoms.

As examples of volatile hydrocarbon-based oils that may be used in the invention, mention may be made of:

volatile hydrocarbon-based oils chosen from hydrocarbon-based oils containing from 8 to 16 carbon atoms, and especially C8-C16 isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched C8-C16 esters and isohexyl neopentanoate, and mixtures thereof. Use may also be made of other volatile hydrocarbon-based oils, such as petroleum distillates, in particular those sold under the name Shell Solt by the company Shell; and volatile linear alkanes, such as those described in patent application DE10 2008 012 457 from the company Cognis;

As examples of nonvolatile hydrocarbon-based oils that may be used in the invention, mention may be made of:

hydrocarbon-based oils of animal origin, such as perhydrosqualene;

hydrocarbon-based plant oils such as liquid triglycerides of fatty acids of 4 to 24 carbon atoms, for instance heptanoic or octanoic acid triglycerides, or wheatgerm oil, olive oil, sweet almond oil, palm oil, rapeseed oil, cottonseed oil, alfalfa oil, poppy oil, pumpkin oil, marrow oil, blackcurrant oil, evening primrose oil, millet oil, barley oil, quinoa oil, rye oil, safflower oil, candlenut oil, passion flower oil, musk rose oil, sunflower oil, corn oil, soybean oil, grapeseed oil, sesame seed oil, hazelnut oil, apricot oil, macadamia oil, castor oil, avocado oil, and caprylic/capric acid triglycerides, for instance those sold by the company Stéarineries Dubois or those sold under the names Miglyol 810, 812 and 818 by the company Dynamit Nobel;

linear or branched hydrocarbons, of mineral or synthetic origin, such as liquid paraffins and derivatives thereof, petroleum jelly, polydecenes, polybutenes, hydrogenated polyisobutene such as Parleam, or squalane;

synthetic ethers containing from 10 to 40 carbon atoms;

synthetic esters, especially of fatty acids, for instance the oils of formula $R_1COOR_2$ in which $R_1$ represents a linear or branched higher fatty acid residue containing from 1 to 40 carbon atoms and $R_2$ represents a hydrocarbon-based chain, which is especially branched, containing from 1 to 40 carbon atoms, with $R_1+R_2 \geq 10$, for instance purcellin oil (cetostearyl octanoate), isononyl isononanoate, isopropyl myristate, isopropyl palmitate, $C_{12}$ to $C_{15}$ alcohol benzoates, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate;

fatty alcohols which are liquid at room temperature, comprising a branched and/or unsaturated carbon chain having from 12 to 26 carbon atoms, such as octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates, such as diethylhexyl carbonate;

acetates;

citrates.

As examples of partially hydrocarbon-based and/or silicone-based fluoro oils, mention may be made of fluorosilicone oils, fluorinated polyethers and fluorosilicones as described in document EP-A-847 752.

As examples of nonvolatile silicone oils, mention may be made of linear or cyclic nonvolatile polydimethylsiloxanes (PDMSs); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and mixtures thereof.

Preferentially, the oil will be chosen from linear or branched nonvolatile hydrocarbons, of mineral or synthetic origin; carbonates; nonvolatile linear polydimethylsiloxanes (dimethicones), and mixtures thereof.

Even more preferentially, the oil will be chosen from polydecenes, hydrogenated polydecenes; carbonates; nonvolatile linear polydimethylsiloxanes (dimethicones), and mixtures thereof.

The oil(s) in the oily phase of the compositions of the invention are preferably present in contents ranging from 45% to 75% by weight and more particularly from 50% to 70% by weight relative to the total weight of the composition.

Solid Fatty Substances

The composition according to the invention comprises at least one solid fatty substance preferably chosen from waxes and pasty fatty substances, and mixtures thereof, and more particularly waxes.

Pasty Fatty Substance

For the purposes of the present invention, the term "pasty fatty substance" (also known as pasty fatty substance) means a lipophilic fatty compound with a reversible solid/liquid change of state, having anisotropic crystal organization in the solid state, and comprising a liquid fraction and a solid fraction at a temperature of 23° C.

In other words, the starting melting point of the pasty compound may be less than 23° C. The liquid fraction of the pasty compound measured at 23° C. may represent 9% to 97% by weight of the compound. This fraction that is liquid at 23° C. preferably represents between 15% and 85% and more preferably between 40% and 85% by weight.

Within the meaning of the invention, the melting point corresponds to the temperature of the most endothermic peak observed in thermal analysis (DSC) as described in Standard ISO 11357-3: 1999. The melting point of a pasty substance or of a wax may be measured using a differential scanning calorimeter (DSC), for example the calorimeter sold under the name MDSC 2920 by the company TA Instruments.

The measurement protocol is as follows:

A sample of 5 mg of pasty substance or wax (depending on the case) placed in a crucible is subjected to a first temperature rise passing from −20° C. to 100° C., at a heating rate of 10° C./minute, then is cooled from 100° C. to −20° C. at a cooling rate of 10° C./minute and finally subjected to a second temperature rise passing from −20° C. to 100° C. at a heating rate of 5° C./minute. During the second temperature rise, the variation in the difference between the power absorbed by the empty crucible and by the crucible containing the sample of pasty substance or wax as a function of the temperature is measured. The melting point of the compound is the temperature value corresponding to the top of the peak of the curve representing the variation in the difference in power absorbed as a function of the temperature.

The liquid fraction by weight of the pasty compound at 23° C. is equal to the ratio of the enthalpy of fusion consumed at 23° C. to the enthalpy of fusion of the pasty compound.

The heat of fusion of the pasty compound is the heat consumed by the compound in order to pass from the solid state to the liquid state. The pasty compound is said to be in the solid state when all of its mass is in the crystalline solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instruments, with a temperature rise of 5° C. or 10° C. per minute, according to standard ISO 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., formed of a liquid fraction and a solid fraction.

The liquid fraction of the pasty compound measured at 32° C. preferably represents from 30% to 100% by weight of the compound, preferably from 50% to 100% and more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The enthalpy of fusion consumed at 32° C. is calculated in the same way as the enthalpy of fusion consumed at 23° C.

The pasty compound is preferably chosen from synthetic compounds and compounds of plant origin. A pasty compound may be obtained via synthesis from starting materials of plant origin.

The pasty compound is advantageously chosen from:

lanolin and derivatives thereof, polyol ethers chosen from pentaerythrityl ethers of a polyalkylene glycol, fatty alkyl ethers of a sugar, and mixtures thereof, the pentaerythrityl ether of polyethylene glycol comprising 5 oxyethylene units (5 OE) (CTFA name: PEG-5 Pentaerythrityl Ether), polypropylene glycol pentaerythrityl ether comprising 5 oxypropylene (5 OP) units (CTFA name: PPG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 pentaerythrityl ether, 46% PPG-5 pentaerythrityl ether and 8% soybean oil,
polymeric or non-polymeric silicone compounds,
polymeric or non-polymeric fluoro compounds,
vinyl polymers, especially:
olefin homopolymers and copolymers,
hydrogenated diene homopolymers and copolymers,
linear or branched homopolymer or copolymer oligomers of alkyl (meth)acrylates preferably containing a $C_8$-$C_{30}$ alkyl group,
homopolymer and copolymer oligomers of vinyl esters containing $C_8$-$C_{30}$ alkyl groups,
homopolymeric and copolymeric oligomers of vinyl ethers containing $C_8$-$C_{30}$ alkyl groups,
liposoluble polyethers resulting from the polyetherification between one or more $C_2$-$C_{100}$ and preferably $C_2$-$C_{50}$ diols,
esters,
and mixtures thereof.

The pasty compound is preferably a polymer, especially a hydrocarbon-based polymer.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of propylene oxide to the alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by AkzoNobel.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol,
the arachidyl propionate sold under the brand name Waxenol 801 by Alzo,
phytosterol esters,
fatty acid triglycerides and derivatives thereof,
pentaerythritol esters,
non-crosslinked polyesters resulting from polycondensation between a linear or branched $C_4$-$C_{50}$ dicarboxylic acid or polycarboxylic acid and a $C_2$-$C_{50}$ diol or polyol,
ester aliphatic esters resulting from the esterification of an aliphatic hydroxycarboxylic acid ester with an aliphatic carboxylic acid. Preferably, the aliphatic carboxylic acid comprises from 4 to 30 and preferably from 8 to carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid containing from 2 to 40 carbon atoms, preferably from 10 to 34 carbon atoms and better still from 12 to 28 carbon atoms, and from 1 to 10 hydroxyl groups, preferably from 1 to 10 hydroxyl groups and better still from 1 to 6 hydroxyl groups.

The aliphatic hydroxycarboxylic acid ester is chosen from:
a) partial or total esters of saturated linear mono-hydroxylated aliphatic monocarboxylic acids;
b) partial or total esters of unsaturated monohydroxylated aliphatic monocarboxylic acids;
c) partial or total esters of saturated monohydroxylated aliphatic polycarboxylic acids;
d) partial or total esters of saturated polyhydroxylated aliphatic polycarboxylic acids;
e) partial or total esters of $C_2$ to $C_{16}$ aliphatic polyols that have reacted with a monohydroxylated or polyhydroxylated aliphatic monocarboxylic or polycarboxylic acid, and mixtures thereof,
esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl/isostearyl/cetyl/stearyl/behenyl dimer dilinoleate (Plandool H or Plandool S), and mixtures thereof,
hydrogenated rosinate esters, such as dilinoleyl dimers of hydrogenated rosinate (Lusplan DD-DHR or DD-DHR from Nippon Fine Chemical);
and mixtures thereof.

Wax(es)

According to a preferred embodiment, the composition according to the invention comprises at least one wax.

The wax under consideration in the context of the present invention is generally a lipophilic compound that is solid at room temperature (25° C.), with a solid/liquid reversible change of state, having a melting point of greater than or equal to 30° C., which may be up to 200° C. and in particular up to 120° C.

In particular, the waxes that are suitable for use in the invention may have a melting point of greater than or equal to 45° C. and in particular greater than or equal to 55° C.

The waxes that may be used in the compositions according to the invention are chosen from waxes that are solid at room temperature, of animal, plant, mineral or synthetic origin, and mixtures thereof.

Examples that may be mentioned include the following hydrocarbon-based waxes comprising a fatty alkyl chain generally containing from 10 to 60 carbon atoms and preferably from 20 to 40 carbon atoms, said chain possibly being saturated or unsaturated, substituted or unsubstituted, and linear, branched or cyclic, preferably saturated and linear:
fatty alcohols that are solid at room temperature (25° C.), such as stearyl alcohol or cetyl alcohol or mixtures thereof,
fatty alcohol esters,
fatty acids,
fatty acid amides,
fatty acid esters including triglycerides,
fatty acid ethers,
ethoxylated fatty alcohols;

ethoxylated fatty acids and the corresponding salts thereof.

Among the fatty alcohols, mention may be made of stearyl alcohol and cetearyl alcohol, or mixtures thereof.

Among the fatty alcohol esters, mention may be made of triisostearyl citrate, ethylene glycol bis(12-hydroxystearate), tristearyl citrate, stearyl octanoate, stearyl heptanoate, trilauryl citrate, and mixtures thereof.

Among the fatty acid esters, mention may be made of ester waxes, monoglycerides, diglycerides and triglycerides.

Ester waxes that may be mentioned include stearyl stearate, stearyl behenate, stearyloctyldodecanol, cetearyl behenate, behenyl behenate, ethylene glycol distearate and ethylene glycol dipalmitate. Use may be made in particular of a $C_{20}$-$C_{40}$ alkyl (hydroxystearyloxy)stearate (the alkyl group containing from 20 to 40 carbon atoms), alone or as a mixture. Such a wax is especially sold under the names "Kester Wax K 82 P®", "Hydroxypolyester K 82 P®" and "Kester Wax K 80 P®" by the company Koster Keunen.

Among the triglyceride waxes, mention may be made more particularly of tribehenin, $C_{18}$-$C_{36}$ triglycerides, and mixtures thereof.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Mention may especially be made, among these waxes, of isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S® by the company Heterene.

Mention may also be made of silicone waxes ($C_{30-45}$ alkyl dimethicone) and fluorinated waxes.

The waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

As microwaxes that may be used in the compositions according to the invention, mention may be made especially of carnauba microwaxes, such as the product sold under the name MicroCare 350® by the company Micro Powders, synthetic microwaxes, such as the product sold under the name MicroEase 114S® by the company Micro Powders, microwaxes consisting of a mixture of carnauba wax and polyethylene wax, such as the products sold under the names Micro Care 300® and 310® by the company Micro Powders, microwaxes consisting of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

Use will be made more particularly of triglyceride waxes and more particularly tribehenine, $C_{18}$-$C_{36}$ triglycerides, and mixtures thereof.

The composition according to the invention may comprise a content of solid fatty substance preferably ranging from 1% to 20% by weight and in particular from 2% to 12% by weight relative to the total weight of the composition.

Hydrophobic Silica Aerogel Particles

According to a particular form of the invention, the compositions according to the invention also contain hydrophobic silica aerogel particles.

The composition according to the invention comprises hydrophobic silica aerogel particles. These are preferably in a dispersion in the aqueous phase of the composition.

Aerogels are ultralight porous materials which were first produced by Kristler in 1932.

They are generally synthesized via a sol-gel process in liquid medium and then dried by extraction of a supercritical fluid. The supercritical fluid most commonly used is supercritical $CO_2$. Drying of this type makes it possible to avoid contraction of the pores and of the material.

Other types of drying also make it possible to obtain porous materials starting from gel, namely (i) drying by freeze drying, which consists in solidifying the gel at low temperature and in then subliming the solvent, and (ii) drying by evaporation. The materials thus obtained are referred to respectively as cryogels and xerogels. The sol-gel process and the various drying operations are described in detail in Brinker C. J. and Scherer G. W., Sol-Gel Science, New York, Academic Press, 1990.

The term "hydrophobic silica" means any silica whose surface is treated with silylating agents, for example with halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

Preferably, the hydrophobic aerogel particles that may be used in the present invention advantageously have a specific surface area per unit mass (SM) ranging from 500 to 1500 $m^2/g$, preferably from 600 to 1200 $m^2/g$ and better still from 600 to 800 $m^2/g$ and/or have an oil absorption capacity measured at the wet point ranging from 5 to 18 ml/g of particles, preferably from 6 to 15 ml/g and better still from 8 to 12 ml/g.

The absorbing capacity measured at the wet point, noted Wp, corresponds to the amount of oil that needs to be added to 100 g of particles in order to obtain a homogeneous paste.

It is measured according to the "wet point" method or the method for determining the oil uptake of a powder according to the principle described in standard NF T 30-022. It corresponds to the amount of oil adsorbed onto the available surface of the powder and/or absorbed by the powder by measurement of the wet point, described below:

An amount m=2 g of powder is placed on a glass plate, and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread over the glass plate without cracks or the formation of lumps. The volume Vs (expressed in ml) of oil used is then noted.

The oil uptake corresponds to the ratio Vs/m.

The hydrophobic silica aerogel particles used according to the present invention are preferably silylated silica (INCI name: silica silylate) aerogel particles.

The preparation of hydrophobic silica aerogel particles that have been surface-modified by silylation is described more fully in U.S. Pat. No. 7,470,725.

Use will be made in particular of aerogel particles of hydrophobic silica surface-modified with trimethylsilyl groups.

The hydrophobic silica aerogel particles that may be used in the present invention advantageously have a size, expressed as the mean diameter (D[0.5]), of less than 1500 μm, and preferably ranging from 1 to 30 μm, preferably from 5 to 25 μm, better still from 5 to 20 μm and even better still from 5 to 15 μm.

The specific surface area per unit mass may be determined by the nitrogen absorption method, known as the BET (Brunauer-Emmett-Teller) method, described in the Journal of the American Chemical Society, vol. 60, page 309, February 1938 and corresponding to international standard ISO 5794/1 (annex D).

The BET specific surface corresponds to the total specific surface of the particles under consideration.

The sizes of the aerogel particles according to the invention may be measured by static light scattering using a commercial particle size analyzer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is in particular described in the publication by Van de Hulst, H. C., Light Scattering by Small Particles, Chapters 9 and 10, Wiley, New York, 1957.

According to an advantageous embodiment, the hydrophobic aerogel particles used in the present invention have a specific surface area per unit mass (SM) ranging from 600 to 800 m$^2$/g and a size, expressed as the volume-mean diameter (D[0.5]), ranging from 5 to 20 μm and better still from 5 to 15 μm.

According to a preferred embodiment, VM-2270 will more particularly be used, the particles of which have a mean size ranging from 5 to 15 microns and a specific surface area per unit mass ranging from 600 to 800 m$^2$/g.

The hydrophobic aerogel particles used in the present invention may advantageously have a tapped density ρ ranging from 0.04 g/cm$^3$ to 0.10 g/cm$^3$ and preferably from 0.05 g/cm$^3$ to 0.08 g/cm$^3$.

In the context of the present invention, this density may be assessed according to the following protocol, known as the tapped density protocol:

40 g of powder are poured into a graduated measuring cylinder and the cylinder is then placed on a Stav 2003 machine from Stampf Volumeter. The cylinder is then subjected to a series of 2500 tapping actions (this operation is repeated until the difference in volume between two consecutive tests is less than 2%); the final volume Vf of tapped powder is then measured directly on the cylinder.

The tapped density is determined by the ratio: mass (m)/Vf, in this instance 40/Vf (Vf being expressed in cm$^3$ and m in g).

According to one embodiment, the hydrophobic aerogel particles used in the present invention have a specific surface area per unit volume SV ranging from 5 to 60 m$^2$/cm$^3$, preferably from 10 to 50 m$^2$/cm$^3$ and better still from 15 to 40 m$^2$/cm$^3$.

The specific surface area per unit volume is given by the relationship:

$$SV = SM \times \rho$$

where ρ is the tapped density expressed in g/cm$^3$ and SM is the specific surface area per unit mass expressed in m$^2$/g, as defined above.

According to a preferred embodiment, the hydrophobic aerogel particles according to the invention have a specific surface area per unit mass (SM) ranging from 500 to 1500 m$^2$/g, preferably from 600 to 1200 m$^2$/g and better still from 600 to 800 m$^2$/g, and have a size, expressed as the mean diameter (D[0.5]), ranging from 1 to 30 μm and/or an oil absorption capacity, measured at the wet point, ranging from 5 to 18 ml/g of particles, preferably from 6 to 15 ml/g and better still from 8 to 12 ml/g.

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit mass ranging from 600 to 800 m$^2$/g.

Mention may also be made of the aerogels sold by Cabot under the references Aerogel TLD 201, Aerogel OGD 201 and Aerogel TLD 203, Enova Aerogel MT 1100 and Enova Aerogel MT 1200.

Use will be made more particularly of the aerogel sold under the name VM-2270 (INCI name: Silica silylate), by the company Dow Corning, the particles of which have an average size ranging from 5 to 15 microns and a specific surface area per unit mass ranging from 600 to 800 m$^2$/g.

The hydrophobic silica aerogel particles are used in a content preferably ranging from 0.05% to 10% by weight, more preferentially from 0.1% to 5% and even more preferentially from 0.5% to 4% by weight relative to the total weight of the composition.

Organopolysiloxane Elastomer

According to a particular form of the invention, the compositions according to the invention also contain at least one organopolysiloxane elastomer.

Preferably, the organopolysiloxane elastomers according to the invention are obtained by an addition reaction (a) of a diorganopolysiloxane containing at least two hydrogen atoms each bonded to a silicon atom, and (b) of a diorganopolysiloxane containing at least two ethylenically unsaturated groups bonded to the silicon atom, in the presence (c) of a platinum catalyst, according to the process described in patent application EP-A-295 886.

According to a particular form of the invention, the organopolysiloxane elastomers are in powder form.

As examples of organopolysiloxane elastomers in powder form, mention may be made of having the INCI name:

Dimethicone/vinyl dimethicone crosspolymer, for instance the commercial products sold under the names Dow Corning 9505 Cosmetic Powder and Dow Corning 9506 Cosmetic Powder by the company Dow Corning.

According to a particular form of the invention, the organopolysiloxane elastomers are mixed with at least one volatile or nonvolatile hydrocarbon-based oil and/or at least one volatile or nonvolatile silicone oil, to form a gel.

As mixtures of oil/non-emulsifying organopolysiloxane elastomer in gel form, use may be made of the products having the following INCI names:

Dimethicone and dimethicone/vinyl dimethicone crosspolymer, for instance the commercial products sold under the names KSG 6 and KSG 16 by the company Shin-Etsu, Cyclopentasiloxane and dimethicone/vinyl dimethicone crosspolymer, for instance the commercial products sold under the names KSG 15 and KSG 24 by the company Shin-Etsu; Dow Corning 9040 Silicone Elastomer Blend by the company Dow Corning;

Dimethicone and dimethicone crosspolymer, for instance the commercial product sold under the name Dow Corning 9041 Silicone Elastomer Blend by the company Dow Corning;

Mineral oil and vinyl dimethicone/lauryl dimethicone crosspolymer, for instance KSG 41 by the company Shin-Etsu;

Isododecane and vinyl dimethicone/lauryl dimethicone crosspolymer, for instance KSG 42 sold by the company Shin-Etsu;

Triethylhexanoin and vinyl dimethicone/lauryl dimethicone crosspolymer, for instance KSG 43 sold by the company Shin-Etsu;

Squalane and vinyl dimethicone/lauryl dimethicone crosspolymer, for instance KSG 44 sold by the company Shin-Etsu;

Use will be made more particularly of the non-emulsifying elastomeric organopolysiloxanes in gel form having the INCI name: Dimethicone and dimethicone crosspolymer, for instance the commercial product sold under the name Dow Corning 9041 Silicone Elastomer Blend by the company Dow Corning.

The organopolysiloxane elastomer is preferably present in the composition in active material concentrations in an active material content of greater than 1.5% by weight, especially ranging from 2% to 8% by weight and more preferentially ranging from 3% to 6% by weight relative to the total weight of the composition.

Presentation Forms

The compositions according to the invention may be in the form of thick creams, a balm, a pomade or a gel whose hardness may vary as a function of the desired application, the area of material to be treated and the desired conditioning.

The compositions according to the invention may especially be conditioned in a jar; in a device equipped with an openwork wall, especially a grille; in a device equipped with a ball applicator ("roll-on"); in the form of wands (sticks). In this regard, they comprise the ingredients generally used in products of this type, which are well known to those skilled in the art.

Beneficial Agents

The amount of beneficial agent present in the particles in accordance with the invention preferably ranges from 0.1% to 80% by weight relative to the weight of the particle, preferably from 1% to 70% by weight, better still from 10% to 60% and even better still from 15% to 50% by weight relative to the total weight of the particle.

The time for release of the beneficial agent will obviously vary according to the nature and intensity of the stimulus.

The total duration for release of the beneficial agent may be modified and will depend greatly on the composition, the content of particles, the nature and especially the chemical nature of the beneficial agent and its concentration in the particles (amount encapsulated in the particle) and the nature and intensity of the stimulus to which the particle containing the beneficial agent will be subjected. The release may equally be instantaneous or last several hours or even several days.

Among the beneficial agents that may be used according to the invention, mention may be made more particularly of:
(i) fatty substances;
(ii) fragrancing substances;
(iii) pharmaceutical active principles;
(iv) cosmetic active agents.

a) Fatty Substances

They may be chosen from the group comprising
(i) natural oils of plant, animal or marine origin,
(ii) mineral oils,
(iii) hydrogenated oils,
(iv) silicone oils,
(v) terpenes,
(vi) squalene,
(vii) saturated or unsaturated fatty acids,
(viii) fatty acid esters,
(x) waxes,
(x) fatty alcohols,
(xi) butters such as shea butter or cocoa butter,
(xii) and mixtures thereof.

b) Fragrancing substances

The term "fragrancing substance" means any ingredient that is capable of giving off a pleasant odor.

Perfumes are compositions especially containing starting materials (generally referred to as perfumery ingredients) described in S. Arctander, Perfume and Flavor Chemicals (Montclair, N.J., 1969), in S. Arctander, Perfume and Flavor Materials of Natural Origin (Elizabeth, N.J., 1960) and in Flavor and Fragrance Materials—1991, Allured Publishing Co., Wheaton, Ill.

They may be synthesis products or natural products, for instance essential oils, absolutes, resinoids, resins, concretes, and/or synthetic products (terpene or sesquiterpene hydrocarbons, alcohols, phenols, aldehydes, ketones, ethers, acids, esters, nitriles or peroxides, which may be saturated or unsaturated, and aliphatic or cyclic).

According to the definition given in international standard ISO 9235 and adopted by the Commission of the European Pharmacopoeia, an essential oil is an odoriferous product generally of complex composition, obtained from a botanically defined plant raw material, either by steam entrainment, or by dry distillation, or via an appropriate mechanical process without heating. The essential oil is generally separated from the aqueous phase via a physical process which does not result in any significant change in the composition.

Among the essential oils that may be used according to the invention, mention may be mode of those obtained from plants belonging to the following botanical families:

Abietaceae or Pinaceae: conifers; Amaryllidaceae; Anacardiaceae; Anonaceae: ylang ylang; Apiaceae (for example Umbelliferae): dill, *angelica*, coriander, sea fennel, carrot, parsley; Araceae; Aristolochiaceae; Asteraceae: yarrow, *artemisia*, camomile, helichrysum; Betulaceae; Brassicaceae; Burseraceae: frankincense; Caryophyllaceae; Canellaceae; Cesalpiniaceae: copaifera (copaiba balsam); Chenopodaceae; Cistaceae: rock rose; Cyperaceae; Dipterocarpaceae; Ericaceae: *gaultheria* (wintergreen); Euphorbiaceae; Fabaceae; Geraniaceae: geranium; Guttiferae; Hamamelidaceae; Hernandiaceae; Hypericaceae: St John's wort; Iridaceae; Juglandaceae; Lamiaceae: thyme, oregano, monarda, savory, basil, marjorams, mints, patchouli, lavenders, sages, catnip, rosemary, hyssop, balm; Lauraceae: ravensara, sweet bay, rosewood, cinnamon, *litsea*; Liliaceae: garlic; lily, lily of the valley, hyacinth, daffodil; Magnoliaceae: *magnolia*; Malvaceae; Meliaceae; Monimiaceae; Moraceae: hemp, hop; Myricaceae; Myristicaceae: nutmeg; Myrtaceae: *eucalyptus*, tea tree, paperbark tree, cajuput, backhousia, clove, myrtle; Oleaceae; Piperaceae: pepper; Pittosporaceae; Poaceae: lemon balm, lemongrass, vetiver; Polygonaceae; Renonculaceae; Rosaceae: roses; Rubiaceae; Rutaceae: all citrus plants; Salicaceae; Santalaceae: sandalwood; Saxifragaceae; Schisandraceae; Styracaceae: benzoin; Thymelaceae: agarwood; Tilliaceae; Valerianaceae: valerian, spikenard; Verbenaceae: lantana, *verbena*; Violaceae; Zingiberaceae: galangal, turmeric, cardamom, ginger; Zygophyllaceae.

Mention may also be made of the essential oils extracted from flowers (lily, lavender, rose, jasmine, ylang ylang, neroli), from stems and leaves (patchouli, geranium, petitgrain), from fruit (raspberry, peach, coriander, aniseed, cumin, juniper), from fruit peel (bergamot, lemon, orange, grapefruit), from roots (*angelica*, celery, cardamom, iris, sweet flag, ginger), from wood (pinewood, sandalwood, gaiac wood, rose of cedar, camphor), from grasses and gramineae (tarragon, rosemary, basil, lemongrass, sage, thyme), from needles and branches (spruce, fir, pine, dwarf pine) and from resins and balms (*galbanum*, elemi, benzoin, myrrh, olibanum, opopanax).

Examples of fragrancing substances are especially: geraniol, geranyl acetate, farnesol, borneol, bornyl acetate, linolool, linalyl acetate, linalyl propionate, linalyl butyrate, tetrahydrolinolool, citronellol, citronellyl acetate, citronellyl formate, citronellyl propionate, dihydromyrcenol, dihydromyrcenyl acetate, tetrahydromyrcenol, terpineol, terpinyl acetate, nopol, nopyl acetate, nerol, neryl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, cis-3-hexenyl acetate, vetiveryl acetate, ethyl acetate, butyl acetate, hexyl acetate, decyl acetate, isoamyl acetate, stearyl acetate, allyl heptanoate, vetiverol, α-hexylcinnamaldehyde, 2-methyl-3-(p-tert-butylphenyl)propanal, 2-methyl-3-(p-isopropylphenyl)propanal, 3-(p-tert-butylphenyl)propanal, 2,4-dimethylcyclohex-3-enylcarboxaldehyde, tricyclodecenyl acetate, tricyclodecenyl propionate, allyl 3-cyclohexylpropionate, ethyl 6-(acetyloxy)hexanoate, allyl caproate, ethyl 2-methylbutyrate, methyl dihydrojasmonate, hexyl salicylate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetrahydropyran, 3-carboxymethyl-2-pentylcyclopentane, 2-n-4-heptylcyclopentanone, 3-methyl-2-pentyl-2-cyclopentenone, menthone, carvone, tagetone, geranyl acetone, n-decanal, n-dodecanal, anisylpropanal, 9-decen-1-ol, cis-3-hexenol, tetrahydro-2-isobutyl-4-methylpyran-4-ol, 3-methyl-5-phenyl-1-pentanol, 3a,6,6,9a-tetramethyldodecahydronaphtho[2,1-b]furan, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepinonitrile, aubepine, heliotropin, coumarin, eugenol, vanillin, diphenyl ether, citral, citronellal, hydroxycitronellal, hexylcinnamal, 2,4-dimethylcyclohex-3-ene-1-carbaldehyde, 2,6-dimethylhept-5-enal, α,α-dimethyl-p-ethylphenylpropanal, 1,3-benzodioxole-5-carboxaldehyde, limonene, damascone, decalactone, nonalactone, 6,6-dimethoxy-2,5,5-trimethylhex-2-ene, 2,4,4,7-tetramethyloct-6-en-3-one, 1-(5,5-dimethyl-1-cyclohexenyl)pent-4-en-1-one, methylheptenone, 4-(cyclopropylmethyl)phenyl methyl ether, 2-methyl-6-methylideneoct-7-en-2-ol, rose oxide, 1-(1,2,3,4,5,6,7,8-octahydro-2,3,8,8-tetramethyl-2-naphthyl)ethan-1-one, 2-acetonaphthone, 2-isopropyl-5-methylcyclohexanone, ionones, methylionones, isomethylionones, solanone, irones, cis-3-hexenol and esters thereof, indane musks, tetralin musks, isochroman musks, macrocyclic ketones, macrolactone musks, aliphatic musks, ethylene brassylate, rose essence, and mixtures thereof.

In general, perfumes are formed from a mixture of perfumery ingredients which may also be classified into head notes, heart notes and base notes.

The three notes correspond to the greater or lesser volatility of the ingredients of which they are composed: highly volatile head note, moderately volatile heart note and sparingly volatile base note.

(i) The head note, also known as the "top" note, is that which is first perceived by the sense of smell as soon as the perfume comes into contact with the keratin material or any substrate. However, it is the note which fades the fastest: it does not "last". It is difficult to express the time of persistence of this note, since it is very variable: from a few minutes to about 10 minutes.

It is essentially fresh and light. All the citrus notes especially fall into this category. In perfumery, they are grouped under the generic term hesperidean notes, which include orange, lemon, grapefruit, bergamot, neroli, etc. Mention will also be made of herbal notes such as lavender, laurel, thyme or rosemary, and aniseed, menthol, aldehyde, etc. notes. Mention will also be made of *eucalyptus* notes.

(ii) The heart note, also occasionally referred to as the "body note", has a persistence which lasts from a few tens of minutes to a few hours, but its main characteristic is that it is not perceived until after a few minutes. Thus, it "starts" just before the head note dies off. It begins to express itself while the head note is gradually fading away. It is represented essentially by floral, fruity or spicy scents: lily of the valley, honeysuckle, violet, *magnolia*, cinnamon, geranium, jasmine, rose, iris, raspberry, peach, etc.

(iii) The base note, also occasionally known as the "bottom note", gives a perfume its "durability", persistence or staying power. It is perceptible several hours, or even several days, or even several weeks after application onto clothing or a perfume blotter or scent strip, depending on the concentration of the perfume.

Examples that will be mentioned include woods, roots, mosses and resins and animal or mineral substances such as opoponax, musks, amber, sandalwood, benzoin, lichen, clove, sage, etc. Mention will also be made of vanilla, patchouli, coumarin, etc. notes.

Needless to say, ingredients belonging to one or more notes may be encapsulated. However, it will be preferred to encapsulate the most volatile ingredients (i.e. the least persistent) belonging to the head and/or heart notes. Among these ingredients, examples that will be mentioned include:

benzyl acetate
geranyl acetate
cis-3-hexenyl acetate
C18 aldehyde or nonalactone
decyl acetate
allyl amyl glycolate (citral)
ethyl acetate
butyl acetate
allyl 3-cyclohexylpropionate
linalyl acetate
phenylethyl alcohol
hexyl acetate
Berryflor or ethyl 6-(acetyloxy)hexanoate
isoamyl acetate allyl caproate
Amarocite or 6,6-dimethoxy-2,5,5-trimethylhex-2-ene
Citral Lemarome N or 3,7-dimethylocta-2,6-dienal
Canthoxal or anisylpropanal
Claritone or 2,4,4,7-tetramethyloct-6-en-3-one
ethyl 2-methylbutyrate
dihydromyrcenol
cis-3-hexenol
Hedione or methyl dihydrojasmonate
L-carvone
allyl heptanoate
limonene
Neobutenone Alpha or 1-(5,5-dimethyl-1-cyclohexenyl)pent-4-en-1-one
Methylheptenone
Toscanol or 4-(cyclopropylmethyl)phenyl methyl ether
Myrcenol Super or 2-methyl-6-methylideneoct-7-en-2-ol
decalactone
stearyl acetate
rose oxide
linalool
Triplal or 2,4-dimethylcyclohex-3-ene-1-carbaldehyde
Melonal or 2,6-dimethylhept-5-enal
1-(1,2,3,4,5,6,7,8-octahydro-2,3,8,8-tetramethyl-2-naphthyl)ethan-1-one
hexylcinnamal
tetrahydro-2-isobutyl-4-methylpyran-4-ol
hexyl salicylate
1,4-dioxacycloheptadecane-5,17-dione
and mixtures thereof.

According to a particular form of the invention, perfumery ingredients with a saturating vapor pressure at 25° C. of greater than or equal to 10.0 Pa will preferably be chosen.

The saturating vapor pressure (or vapor tension) is the pressure at which the gaseous phase of a substance is in equilibrium with its liquid or solid phase at a given temperature in a closed system. Calculation of the saturating vapor pressure may be performed using the following formula:

$$\ln\frac{p_{sat}}{p_0} = \frac{M.L_v}{R}\left(\frac{1}{T_0} - \frac{1}{T}\right)$$

with:
$T_0$: boiling point of the substance at a given pressure $p_0$, in degrees Kelvin,
$p_{sat}$: saturating vapor pressure, in the same unit as $p_0$
M: molar mass of the substance, in kg/mol
$L_v$: latent heat of vaporization of the substance, in joules/kg
R: ideal gas constant, equal to 8.31447 J/K/mol
T: temperature of the vapor, in K.

Preferably, the fragrancing substances with a saturating vapor pressure at 25° C. of greater than or equal to 10 Pa represent an amount ranging from 50% to 100% by weight, preferably from 60% to 100% by weight, more preferentially from 70% to 100% by weight and better still from 80% to 100% by weight relative to the total weight of the fragrancing substances present in the particles of the invention.

c) Pharmaceutical Active Principles

The term "pharmaceutical active principle" means a molecule or a mixture of molecules which has a curative and/or prophylactic therapeutic effect, which can be administered by spraying.

d) Cosmetic Active Agents

The term "cosmetic active agent" means any molecule which has a hygiene, care, makeup or coloring effect contributing toward the improvement well-being and/or enhancement or modification of the appearance of the human keratin material onto which said composition is applied.

Among the cosmetic active agents that may be applied to human keratin materials such as the skin, the lips, the scalp, the hair, the eyelashes or the nails, examples that may be mentioned, alone or as mixtures, include:
vitamins and derivatives or precursors thereof, alone or as mixtures;
antioxidants;
cleaning agents such as surfactants;
dyestuffs;
conditioning agents;
agents for relaxing and/or straightening and/or shaping the hair;
free-radical scavengers;
photoprotective agents such as organic or mineral UV-screening agents;
self-tanning agents;
anti-glycation agents;
calmatives;
hair-removing agents;
deodorant agents;
antiperspirant agents;
NO-synthase inhibitors;
agents for stimulating fibroblast proliferation;
agents for stimulating keratinocyte proliferation;
dermo-relaxing agents,
refreshing agents;
tensioning agents,
matt-effect agents;
skin-shine counteractants;
antiseborrhea agents;
greasy-hair counteractants;
depigmenting agents;
pro-pigmenting agents;
keratolytic agents;
desquamating agents;
moisturizers;
antimicrobial agents;
slimming agents;
agents that act on the energy metabolism of cells;
insect repellents;
substance P or CGRP antagonists;
hair-loss counteractants;
antiwrinkle agents;
antiaging agents;
antidandruff agents.

Among these cosmetic active agents, preference will be given most particularly, alone or as mixtures, to:
photoprotective agents such as UV-screening agents, in particular organic UV-screening agents;
skin-shine counteractants;
antiseborrhea agents;
greasy-hair counteractants;
deodorant agents;
antiperspirant agents;
refreshing agents;
matt-effect agents;
antimicrobial agents;
antidandruff agents.

According to a particularly preferred form of the invention, the beneficial agent(s) present in the particles will be chosen from fragrancing substances.

According to an even more particularly preferred form of the invention, the fragrancing substances present in the particles are chosen from heart notes and/or head notes so as to be able both to compensate for their loss throughout the day and to afford an additional freshness effect throughout the day in response to perspiration or to atmospheric humidity or humidity provided, for example, by misters.

According to a particular form of the invention, the composition will contain a) particles containing at least one fragrancing substance and b) at least one fragrancing substance in free form, which may be identical to or different from the fragrancing substance present in said particles.

Said fragrancing substances in free form may be chosen from those mentioned previously.

According to another particular form of the invention, the composition exclusively contains the fragrancing substance(s) in the encapsulation particles. In other words, all of the ingredients for fragrancing that are present in the composition are contained in the particles.

The composition may also comprise other ingredients in free form (not encapsulated or imprisoned in the particles of the invention) used commonly in cosmetic compositions. Such ingredients may be chosen from antioxidants, preserving agents, cosmetic active agents such as those mentioned previously, fragrancing substances such as those described previously, surfactants, spreading agents, wetting agents, dispersants, antifoams, neutralizers, stabilizers, polymers and especially liposoluble film-forming polymers, and mixtures thereof.

Needless to say, those skilled in the art will take care to select this or these optional additional compound(s) and/or the amounts thereof so that the advantageous properties of the composition for the use according to the invention are not, or are not substantially, adversely affected by the envisaged addition.

The compositions according to the invention may be in any form that is acceptable and common for a composition in soft solid form.

A person skilled in the art can choose the appropriate composition, and also its method of preparation, on the basis of his general knowledge, taking into account first the nature of the constituents used, especially their solubility in the support, and secondly the application envisaged for the composition.

According to another particular form of the invention, the compositions according to the invention may be in the form of a hygiene product, in particular of deodorants and/or antiperspirants in which the composition comprises at least one deodorant active agent and/or at least one antiperspirant active agent, in free form and/or in encapsulated form. More particularly, the particles comprise at least one fragrancing substance. Even more particularly, the compositions will also contain at least one fragrancing substance in free form, which may be identical to or different from the fragrancing substance(s) present in the particles.

Antiperspirant Active Agent

The term "antiperspirant active agent" means a compound which, by itself, has the effect of reducing the flow of sweat and/or of reducing the sensation on the skin of moisture associated with human sweat and/or of partially or totally absorbing human sweat.

Among the antiperspirant active agents that may be mentioned are aluminum and/or zirconium salts such as aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, alum salts, aluminum sulfate, aluminum zirconium octachlorohydrate, aluminum zirconium pentachlorohydrate, aluminum zirconium tetrachlorohydrate, aluminum zirconium trichlorohydrate and more particularly the aluminum chlorohydrate in activated or nonactivated form sold by the company Reheis under the name Microdry Aluminum Chlorohydrate® or by the company Guilini Chemie under the name Aloxicoll PF 40. Aluminum and zirconium salts are, for example, the product sold by the company Reheis under the name Reach AZP-908-SUF®, "activated" aluminum salts, for example the product sold by the company Reheis under the name Reach 103 or by the company Westwood under the name Westchlor 200.

Preferably, the cosmetic composition comprises aluminum chlorohydrate as antiperspirant active agent.

As other antiperspirant active agent, mention may be made of expanded perlite particles such as those obtained by the expansion process described in U.S. Pat. No. 5,002,698.

The perlites that may be used according to the invention are generally aluminosilicates of volcanic origin and have the composition:

70.0%-75.0% by weight of silica $SiO_2$
12.0%-15.0% by weight of aluminum oxide $Al_2O_3$
3.0%-5.0% of sodium oxide $Na_2O$
3.0%-5.0% of potassium oxide $K_2O$
0.5%-2% of iron oxide $Fe_2O_3$→
0.2%-0.7% of magnesium oxide MgO
0.5%-1.5% of calcium oxide CaO
0.05%-0.15% of titanium oxide $TiO_2$.

Preferably, the perlite particles used will be ground; in this case, they are known as Expanded Milled Perlite (EMP). They preferably have a particle size defined by a median diameter D50 ranging from 0.5 to 50 μm and preferably from 0.5 to 40 μm.

Preferably, the perlite particles used have a loose bulk density at 25° C. ranging from 10 to 400 kg/m³ (standard DIN 53468) and preferably from 10 to 300 kg/m³.

Preferably, the expanded perlite particles according to the invention have a water absorption capacity, measured at the wet point, ranging from 200% to 1500% and preferably from 250% to 800%.

The wet point corresponds to the amount of water which has to be added to 100 g of particle in order to obtain a homogeneous paste. This method is directly derived from the oil uptake method applied to solvents. The measurements are taken in the same manner by means of the wet point and the flow point, which have, respectively, the following definitions:

Wet point: weight, expressed in grams per 100 g of product, corresponding to the production of a homogeneous paste during the addition of a solvent to a powder.

Flow point: mass expressed in grams per 100 g of product above which the amount of solvent is greater than the capacity of the powder to retain it. This is reflected by the production of a more or less homogeneous mixture which flows over the glass plate.

The wet point and the flow point are measured according to the following protocol:

Protocol for Measuring the Water Absorption

1) Equipment used

Glass plate (25×25 mm)
Spatula (wooden shaft and metal part, 15×2.7 mm)
Silk-bristled brush
Balance 2) Procedure The glass plate is placed on the balance and 1 g of perlite particles is weighed out. The beaker containing the solvent and the sampling pipette is placed on the balance. The solvent is gradually added to the powder, the whole being regularly blended (every 3 to 4 drops) by means of the spatula.

The mass of solvent needed to obtain the wet point is noted. Further solvent is added and the mass which makes it possible to reach the flow point is noted. The average of three tests will be determined.

The expanded perlite particles sold under the trade names Optimat 1430 OR or Optimat 2550 by the company World Minerals will be used in particular.

Deodorant Active Agents

The term "deodorant active agent" refers to any substance that is capable of masking, absorbing, improving and/or reducing the unpleasant odor resulting from the decomposition of human sweat by bacteria.

The deodorant active agents may be bacteriostatic agents or bactericides that act on underarm odor microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts; polyols such as those of glycerol type, 1,3-propanediol (Zemea Propanediol® sold by DuPont Tate & Lyle Bio Products), 1,2-decanediol (Symclariol® from the company Symrise), glycerol derivatives, for instance caprylic/capric glycerides (Capmul MCM® from Abitec), glyceryl caprylate or caprate (Dermosoft GMCY® and Dermosoft GMC®, respectively from Straetmans), polyglyceryl-2 caprate (Dermosoft DGMC® from Straetmans), biguanide derivatives, for instance polyhexamethylene biguanide salts; chlorhexidine and salts thereof; 4-phenyl-4,4-dimethyl-2-butanol (Symdeo MPP® from Symrise); cyclodextrins; chelating agents such as Tetrasodium Glutamate Diacetate (CAS #51981-21-6) sold under the trade name Dissolvine GL-47-S® from AkzoNobel, EDTA (ethylenediaminetetraacetic acid) and DPTA (1,3-diaminopropanetetraacetic acid).

Among the deodorant active agents in accordance with the invention, mention may also be made of:
  zinc salts, such as zinc salicylate, zinc phenolsulfonate, zinc pyrrolidonecarboxylate (more commonly known as zinc pidolate), zinc sulfate, zinc chloride, zinc lactate, zinc gluconate, zinc ricinoleate, zinc glycinate, zinc carbonate, zinc citrate, zinc chloride, zinc laurate, zinc oleate, zinc orthophosphate, zinc stearate, zinc tartrate, zinc acetate or mixtures thereof;
  odor absorbers such as zeolites, especially silver-free metal zeolites, cyclodextrins, metal oxide silicates such as those described in patent application US 2005/063 928; metal oxide particles modified with a transition metal, as described in patent applications US 2005/084 464 and US 2005/084 474, aluminosilicates such as those described in patent application EP 1 658 863, chitosan-based particles such as those described in patent U.S. Pat. No. 6,916,465;
  sodium bicarbonate;
  salicylic acid and derivatives thereof such as 5-n-octanoylsalicylic acid;
  alum;
  triethyl citrate;

The deodorant active agents may preferably be present in the compositions according to the invention in weight proportions of from 0.01% to 10% by weight relative to the total weight of the composition.

The invention also relates to a cosmetic process for treating body odor and optionally human perspiration, which consists in applying to a keratin material a composition comprising particles as defined previously; said composition comprising at least one deodorant active agent and/or at least one antiperspirant active agent in free form and/or in encapsulated form.

The invention is illustrated in greater detail in the examples that follow.

EXAMPLES OF PREPARING PARTICLES WITH RELEASE OF PERFUME

Example A

Capsules were prepared using the following composition:

| | Composition | | | |
|---|---|---|---|---|
| | Hydrophobically modified starch | Water-soluble polysaccharide | Fragrance* | Water |
| Example A | Amidon Capsul ® from National Starch 110 g | Potato maltodextrin MD 20 P from Avebe 110 g | 55 g | 225 g |

*The perfume used has the following composition:

| Ingredients | Amount in g |
|---|---|
| Isopropyl myristate | 20.5 |
| Methyl dihydrojasmonate | 15 |
| 2-Phenylethanol | 8 |
| 1-(1,2,3,4,5,6,7,8-Octahydro-2,3,8,8-tetramethyl-2-naphthyl)ethan-1-one | 8 |
| Hexylcinnamal | 6 |
| Tetrahydro-2-isobutyl-4-methylpyran-4-ol | 6 |
| Hexyl salicylate | 6 |
| Benzyl acetate | 5 |
| 1,4-Dioxacycloheptadecane-5,17-dione | 5 |
| 3-Methyl-5-phenyl-1-pentanol | 5 |
| Dihydromyrcenol | 4 |
| Orange terpenes 0.05% B H T (limonene >95%) | 4 |
| 2-Acetonaphthone | 2 |
| 3a,6,6,9a-Tetramethyldodecahydronaphtho[2,1-b]furan | 1 |
| α,α-Dimethyl-p-ethylphenylpropanal | 1 |
| 1,3-Benzodioxole-5-carboxaldehyde | 1 |
| 2-Isopropyl-5-methylcyclohexanone | 1 |
| 1-Phenylethyl acetate | 0.8 |
| 2,6-Dimethylhept-5-enal (Melonal) | 0.5 |
| 2,4-Dimethylcyclohex-3-ene-1-carbaldehyde (Triplal) | 0.2 |

Process for Preparing the Emulsion

Potato maltodextrin MD20P and Amidon Capsul® (sodium salt of starch octenyl succinate) were mixed in water until dissolved, the perfume was then added and the whole was emulsified with a Heidolph Diax 900 Ultra-Turrax disperser (motor power 900 W with an electronically controlled speed of 8000 to 26 000 rpm) at the maximum power for 4 minutes.

Drying Procedure for Obtaining Spherical Particles

The emulsion obtained was then homogenized at a pressure of 30 bar using a high-pressure pump and then sprayed in an atomization chamber using a nozzle simultaneously with a stream of $CO_2$ (30 bar, 45° C.) which was circulated continuously at a flow rate of about 500 g/min to remove the water. The dried powder was retained on a filter located at the base of the atomization chamber, and then collected after depressurization. 270 g of spherical microcapsules are thus obtained in the form of a fine white powder of particle size

| | Measured characteristics of the capsules | | | |
|---|---|---|---|---|
| | Amount of encapsulated perfume (%) | Amount of free perfume (%) | Poured powder density | Absolute density |
| Example A | 19.8 | >0.1 | 484 | 1.12 |

Examples B to H

According to the process described in Example A, the following capsules were prepared:

| | Composition | | | |
|---|---|---|---|---|
| | Hydrophobically modified starch | Water-soluble polysaccharide | Polymer of Example A | Water |
| Example B | Amidon Capsul ® from National Starch 110 g | Maltodextrin MD 120 from Tereos 110 g | 55 g | 225 g |
| Example C | Amidon Capsul ® from National Starch 110 g | Maltodextrin MD 170 from Tereos 110 g | 55 g | 225 g |
| Example D | Amidon Capsul ® from National Starch 110 g | Maltodextrin MD 190 from Tereos 110 g | 55 g | 225 g |
| Example E | Amidon Capsul ® from National Starch 110 g | Potato maltodextrin MD 20 P from Avebe 110 g | 105 g | 225 g |
| Example F | Amidon Capsul ® from National Starch 154 g (70%) | Potato maltodextrin MD 20 P from Avebe 66 g | 55 g | 225 g |
| Example G | Amidon Capsul ® from National Starch 66 g (30%) | Potato maltodextrin MD 20 P from Avebe 154 g | 55 g | 225 g |
| Example H | Amidon Capsul ® from National Starch 110 g | Glucose syrup Glucodry G290 from Tereos 110 g | 55 g | 225 g |

| | Measured characteristics of the capsules | | | |
|---|---|---|---|---|
| Examples | Amount of encapsulated perfume (%) | Amount of free perfume (%) | Poured powder density (g/l) | Absolute density |
| Example B | 19.3 | <0.1 | 568 | 1.14 |
| Example C | 19.4 | <0.1 | 490 | 1.16 |
| Example D | 19.9 | <0.1 | 537 | 1.11 |
| Example E | 38 | 0.8 | 482 | 1.08 |
| Example F | 21.0 | 0.2 | 595 | 1.11 |
| Example G | 20.7 | 0.2 | 521 | 1.15 |
| Example H | 19.2 | 0.1 | 568 | 1.12 |

Comparative Example I

Capsules having the same composition as Example A as described above were prepared according to the process of Example 1 of U.S. Pat. No. 6,200,949 comprising drying by spray-drying (atomization) of the emulsion.

The emulsion is dried by spray-drying using a Bowen Lab Model Dryer machine using air with a flow rate of 420 m³/h at a temperature of 204° C. and an external temperature of 93° C. and a turbine speed of 50 000 rpm.

Morphological aspect of the particles obtained: polymorphous and formation of aggregates Comparative Example J Capsules having the same composition as Example A as described above were prepared according to the process of Example 1 of patent U.S. Pat. No. 5,508,259 comprising drying by spray-drying (atomization) of the emulsion.

The mixture was dried by spray-drying with a CCM Sulzer machine at an emulsion flow rate of 50 kg/h, air at a flow rate of 320 m³/h at 350° C. and 0.45 bar.

Morphological aspect of the particles obtained: polymorphous and formation of aggregates

| | Measured characteristics of the capsules | | | |
|---|---|---|---|---|
| Composition | Amount of encapsulated perfume (%) | Amount of free perfume (%) | Poured powder density | Absolute density |
| Example I (outside the invention) | 18.3 | 2.7 | 259 g/l | 1.16 |
| Example J (outside the invention) | 11.2 | 1.7 | 269 g/l | 1.12 |

Example 1: Deodorant and Antiperspirant Product

An antiperspirant anhydrous soft solid composition having the following composition was prepared:

| Phase | Ingredients | (% by weight) |
|---|---|---|
| A | Tribehenin (Syncrowax HRC-PA ®) | 5.6 |
| | C18-36 Acid Triglycerides (Syncrowax HGLC-PA ®) | 1.4 |
| | Aluminum zirconium tetrachlorohydrex glycine (Reach AZP-908 ®) | 18.7 |
| B | Hydrogenated polydecene (Silkflo 366 Polydecene ®) | 24.6 |
| | PPG-14 butyl ether | 1.9 |
| | Dimethicone (viscosity: 10 cSt) (Belsil DM 10 ®) | 37.2 |

-continued

| Phase | Ingredients | (% by weight) |
|---|---|---|
| C | Dimethicone (and) dimethicone crosspolymer (Dow Corning 9041 Silicone Elastomer Blend ®) | 1.9 |
| D | Silica silylate (Dow Corning VM-2270 Aerogel Fine Particles ®) | 1.9 |
| E | Calcium hydroxide | 0.5 |
| F | Capsules of perfume of Example A | 6.3 |
| | Total | 100.00 |

Preparation Method

The two waxes (phase A) were weighed out and melted in a tank at 95° C.

The oils and the aluminum salts (phase B) were then mixed separately using a spatula at room temperature and this phase B was divided into three.

The silicone elastomer (phase C) was added to one third of phase B and the whole was homogenized with a spatula at room temperature until a homogeneous mixture was obtained.

The silica aerogel (phase D) was then weighed out in a large capsule and added cautiously to a second third of phase B with mixing until a smooth gel was obtained.

The calcium hydroxide (phase E) was also weighed out and introduced into the final third of the remaining phase B with Ultra-Turrax stirring at 1300 rpm for 15 minutes.

With the tank open, the three preceding preparations were added to the molten waxes and the resulting mixture was homogenized using paddles and a turbine (low speed) for 15 minutes at 90° C.

The perfume capsules of Example A were finally incorporated, with the tank open, and the whole was then homogenized with stirring for 5 minutes and left to cool. A white soft solid gel was thus obtained.

Evaluation Protocol

About 0.2 g of the composition of Example 1 was deposited uniformly onto a perfume blotter (reference from Granger Veyron: 40140BCSI of size 4 cm×14 cm). After 1 minute, it was checked to ensure that it had no perfume odor. Perspiration was then simulated by adding about 0.1 g of water (three sprays) onto the deposited composition. After waiting for 60 seconds, the blotter was smelled again. A strong odor of perfume correctly corresponding to the encapsulated perfume was noted. 4 hours later, the same amount of water was sprayed on again and intense release of perfume was noted. 20 hours later, a re-evaluation was performed in the same manner, and the release of perfume was again noted.

Examples C1 and C2

In a manner similar to that of Example 1, antiperspirant anhydrous soft solids having the following compositions were prepared:

Example C1

| Phase | Ingredients | (% by weight) |
|---|---|---|
| A | Tribehenin | 5.6 |
| | C18-36 Acid Triglycerides | 1.4 |

Example C1

| Phase | Ingredients | (% by weight) |
|---|---|---|
| B | Aluminum zirconium tetrachlorohydrex glycine | 18.7 |
| | Hydrogenated polydecene | 24.6 |
| | PPG-14 butyl ether | 1.9 |
| | Dimethicone | 37.2 |
| C | Dimethicone (and) dimethicone crosspolymer | 1.9 |
| D | Silica silylate | 1.9 |
| E | Calcium hydroxide | 0.5 |
| F | Capsules of perfume of Example I | 6.3 |
| | Total | 100.00 |

Example C2

| Phase | Ingredients | (% by weight) |
|---|---|---|
| A | Tribehenin | 5.6 |
| | C18-36 Acid Triglycerides | 1.4 |
| B | Aluminum zirconium tetrachlorohydrex glycine | 18.7 |
| | Hydrogenated polydecene | 24.6 |
| | PPG-14 butyl ether | 1.9 |
| | Dimethicone | 37.2 |
| C | Dimethicone (and) dimethicone crosspolymer | 1.9 |
| D | Silica silylate | 1.9 |
| E | Calcium hydroxide | 0.5 |
| F | Capsules of perfume of Example J | 6.3 |
| | Total | 100.00 |

Evaluation Protocol:

About 0.2 g of composition was deposited onto a perfume blotter (reference from Granger Veyron: 40140BCSI of size 4 cm×14 cm) and spread out homogeneously using a dry finger. The feel of the product was noted. After 1 minute, the perfume odor intensity was evaluated. Perspiration was then simulated by adding about 0.1 g of water (three sprays) onto the deposited composition. After waiting for 60 seconds, the blotter was smelled again.

| Soft Solid | Feel | Odor intensity BEF | Odor intensity AFT |
|---|---|---|---|
| Example 1 | Sparingly granular | Odorless | Very strong perfume odor |
| Example C1 | Granular | Strong perfume odor | Very strong perfume odor |
| Example C2 | Granular | Strong perfume odor | Strong perfume odor |

BEF = before addition of water;
AFT = after addition of water

It was thus observed at $T_0$ that the soft solid of Example 1 comprising the perfume capsules according to the invention has no odor before the addition of water, in contrast with Examples C1 and C2 (outside the invention), which shows that the perfume capsules in Examples C1 and C2 are not leaktight even before the addition of water. It was also observed that the feel of the soft solid of Example 1 was significantly less granular than that of Example C1 or C2.

It was also observed that the soft solid of Example, 1 after stimulation with water, led to a very intense odor, which demonstrates substantial release of perfume in response to the water stimulus.

The composition applied to the armpits leaves a deposit on the skin which gives off a perfume odor. The perfume is released in the course of the day when the capsules are in contact with perspiration.

Example 2: Deodorant and Antiperspirant Product

An antiperspirant anhydrous soft solid composition having the following composition was similarly prepared:

| Phase | Ingredients | (% by weight) |
|---|---|---|
| A | Tribehenin (Syncrowax HRC-PA ®) | 5.7 |
|   | C18-36 Acid Triglycerides (Syncrowax HGLC-PA ®) | 1.4 |
| B | Aluminum zirconium tetrachlorohydrex glycine (Reach AZP-908 ®) | 19.0 |
|   | Hydrogenated polydecene (Silkflo 366 Polydecene ®) | 24.9 |
|   | PPG-14 butyl ether | 1.9 |
|   | Dimethicone (viscosity: 10 cSt) (Belsil DM 10 ®) | 37.6 |
| C | Dimethicone (and) dimethicone crosspolymer (Dow Corning 9041 Silicone Elastomer Blend ®) | 1.9 |
| D | Silica silylate (Dow Corning VM-2270 Aerogel Fine Particles ®) | 1.9 |
| E | Calcium hydroxide | 0.5 |
| F | Capsules of perfume of Example A | 5.0 |
|   | Free perfume A | 0.2 |
|   | Total | 100.00 |

The capsules of perfume of Example A may be replaced with the capsules of Examples B to H described previously.

The composition obtained has a hardness of 21 kPa measured according to the protocol described previously.

The composition applied to the armpits leaves a deposit on the skin which gives off a perfume odor. The perfume is released in the course of the day when the capsules are in contact with perspiration.

The intensity of the perfume odor on the skin was evaluated at T0, T2h, T4h and T6h after application of the composition.

0.2 g of the composition of Example 2 was applied homogeneously to the skin. After 1 minute, the intensity of the perfume odor was evaluated (APPLICATION), and was graded from 0 to 10. 2, 4 and 6 hours later, the intensity of the odor was re-evaluated (BEF) before adding about 0.1 g of water (three sprays) to the composition applied to the skin. After waiting for 30 seconds, the intensity of the odor was evaluated (AFT).

It was thus observed at T0 that the composition of Example 2 has a moderate odor which decreases greatly, being weak at 2 hours after application. It was also observed that the spraying of water onto the deposit at T2h, T4h and T6h leads to an increase in the odor intensity (especially of the fresh notes), which demonstrates substantial release of perfume.

Example 3: Deodorant and Antiperspirant Product

An antiperspirant anhydrous soft solid composition having the following composition was similarly prepared:

| Phase | Ingredients | (% by weight) |
|---|---|---|
| A | Tribehenin (Syncrowax HRC-PA ®) | 5.8 |
|   | C18-36 Acid Triglycerides (Syncrowax HGLC-PA ®) | 1.5 |
| B | Aluminum zirconium tetrachlorohydrex glycine (Reach AZP-908 ®) | 19.4 |
|   | Hydrogenated polydecene (Silkflo 366 Polydecene ®) | 25.5 |
|   | PPG-14 butyl ether | 1.9 |
|   | Dimethicone (viscosity: 10 cSt) (Belsil DM 10 ®) | 38.4 |
| C | Dimethicone (and) dimethicone crosspolymer (Dow Corning 9041 Silicone Elastomer Blend ®) | 1.9 |
| D | Silica silylate (Dow Corning VM-2270 Aerogel Fine Particles ®) | 1.9 |
| E | Calcium hydroxide | 0.5 |
| F | Capsules of perfume of Example A | 2.4 |
|   | Free perfume A | 0.8 |
|   | Total | 100.00 |

The capsules of perfume of Example A may be replaced with the capsules of Examples B to H described previously.

The composition obtained has a hardness of 16 kPa measured according to the protocol described previously.

The intensity of the perfume odor on the skin was evaluated at T0, T2h, T4h and T6h after application of the composition according to the protocol described in Example 2.

| Product | Odor intensity T0 APPLICATION | Odor intensity T2 h BEF | AFT | Δ | Odor intensity T4 h BEF | AFT | Δ | Odor intensity T6 h BEF | AFT | Δ |
|---|---|---|---|---|---|---|---|---|---|---|
| Example 2 | 5.0 | 2.5 | 5.5 | 3 | 3.5 | 5.5 | 2.0 | 2.5 | 5.0 | 2.5 |

BEF = before addition of water;
AFT = after addition of water
Δ = amplitude of difference in olfactory intensity (BEF − AFT)
Scale of perfume odor intensity: 0 to 10 (0 = odorless; 10 = very intense/saturated odor).

| | Odor intensity T0 | Odor intensity T2 h | | | Odor intensity T4 h | | | Odor intensity T6 h | | |
|---|---|---|---|---|---|---|---|---|---|---|
| Product | APPLICATION | BEF | AFT | Δ | BEF | AFT | Δ | BEF | AFT | Δ |
| Example 3 | 7.0 | 5.0 | 7.0 | 2 | 3.5 | 6.25 | 2.75 | 3.25 | 4.75 | 1.5 |

It was thus observed at T0 that the composition of Example 3 has a strong odor which decreases, being moderate at 2 hours after application. It was also observed at each check time (T2h, T4h and T6h) that the spraying of water onto the product leads to an increase in the odor intensity (especially of the fresh notes), which demonstrates substantial release of perfume.

The invention claimed is:
1. An anhydrous composition comprising:
   1) particles comprising a core containing at least one beneficial agent, wherein the at least one beneficial agent is at least one fragrancing substance, and an envelope surrounding the core;
   said envelope comprising at least one hydrophobically modified polysaccharide selected from the group consisting of starch ($C_5$-$C_{20}$) alkenyl succinates and at least one water-soluble carbohydrate which is a maltodextrin;
   said particles are spherical, have a number-mean diameter ranging from 1 to 30 μm and a volume-mean diameter ranging from 5 to 150 μm; and
   said particles simultaneously having a poured powder density ranging from 300.0 g/l to 600.0 g/l and an absolute density of greater than 1.0; and
   2) at least one fatty phase comprising at least one solid fatty substance and at least one oil;
   said composition having a hardness measured at 32° C. at a humidity of 40% ranging from 15 kPa to 150 kPa; and
   wherein said particles are obtained according to a process comprising at least the following steps: an aqueous solution formed from a mixture of the water-soluble carbohydrate and of the hydrophobically modified polysaccharide is obtained, then the beneficial agent is added and the whole mixture is stirred so as to form an emulsion;
   said emulsion thus formed is homogenized at high pressure at a pressure ranging from 10 to 200 bar;
   said emulsion is sprayed in a drying chamber; and
   the water is extracted for a time not exceeding 3 hours so as to obtain said particles.
2. The composition as claimed in claim 1, comprising a physiologically acceptable medium.
3. The composition as claimed in claim 1, in which the particles have a number-mean diameter ranging from 2 to 15 μm and a volume-mean diameter ranging from 10 to 100 μm.
4. The composition as claimed in claim 1, in which the hydrophobically modified polysaccharide is sodium starch octenyl succinate.
5. The composition as claimed in claim 1, in which the hydrophobically modified polysaccharide represents from 20% to 90% by weight relative to the total weight of the envelope of the particles.
6. The composition as claimed in claim 1, in which the maltodextrin has a dextrose equivalent ranging from 4 to 20.
7. The composition as claimed in claim 1, in which the at least one water-soluble carbohydrate represents from 10% to 80% by weight relative to the total weight of the envelope of the particles.
8. The composition as claimed in claim 1, in which the envelope of the particles with release of the beneficial agent is formed from the at least one starch ($C_5$-$C_{20}$)alkenyl succinate and from the maltodextrin with a dextrose equivalent ranging from 12 to 20.
9. The composition as claimed in claim 1, in which the envelope of the particles with release of the beneficial agent is formed from
   a) the at least one starch ($C_5$-$C_{20}$)alkenyl succinate in an amount ranging from 20% to 90% by weight relative to the total weight of the envelope of the particles and
   b) the maltodextrin with a dextrose equivalent ranging from 4 to 20 in an amount ranging from 10% to 80% by weight by weight relative to the total weight of the envelope of the particles.
10. The composition as claimed in claim 1, in which the particles comprise the at least one fragrancing substance with a saturating vapor pressure at 25° C. of greater than or equal to 10.0 Pa and said fragrancing substance represents from 50% to 100% by weight relative to the total weight of the fragrancing substance present in the particles.
11. The composition as claimed in claim 1, wherein the composition further comprises the at least one fragrancing substance in free form other than in the particles, which is identical to or different from the fragrancing substance present in said particles.
12. The composition as claimed in claim 1, which exclusively contains the at least one fragrancing substance encapsulated in the particles.
13. The composition as claimed in claim 1, further comprising at least one deodorant active agent and/or at least one antiperspirant active agent in free form other than in the particles and/or in encapsulated form.
14. A process for fragrancing a human keratin material, which comprises applying to said human keratin material the composition as claimed in claim 1.
15. A consumer product, which is formed from the composition as defined as claimed in claim 1.
16. The composition as claimed in claim 1, which contains less than 5% by weight of water.
17. The composition as claimed in claim 1, which contains less than 2% by weight of water.
18. The composition as claimed in claim 1, which contains less than 1% by weight of water.
19. The composition as claimed in claim 1, which contains less than 0.5% by weight of water.

* * * * *